US007598341B2

(12) United States Patent
Hanahan et al.

(10) Patent No.: US 7,598,341 B2
(45) Date of Patent: Oct. 6, 2009

(54) MOLECULES THAT SELECTIVELY HOME TO VASCULATURE OF PREMALIGNANT OR MALIGNANT LESIONS OF THE PANCREAS AND OTHER ORGANS

(75) Inventors: Douglas Hanahan, San Francisco, CA (US); Erkki Ruoslahti, Rancho Santa Fe, CA (US); Johanna A. Joyce, New York, NY (US); Pirjo Laakkonen, Helsinki (FI)

(73) Assignees: Burnham Institue for Medical Research, La Jolla, CA (US); The Regents of the Universtiy of California, Oakland, CA (US)

( * ) Notice: Subject to any disclaimer, the term of this patent is extended or adjusted under 35 U.S.C. 154(b) by 162 days.

(21) Appl. No.: 10/977,367

(22) Filed: Oct. 29, 2004

(65) Prior Publication Data

US 2005/0245445 A1 Nov. 3, 2005

Related U.S. Application Data

(60) Provisional application No. 60/516,118, filed on Oct. 31, 2003.

(51) Int. Cl.
C07K 5/00 (2006.01)
C07K 14/00 (2006.01)

(52) U.S. Cl. ............... 530/300; 530/350; 530/329; 530/324

(58) Field of Classification Search ............ None
See application file for complete search history.

(56) References Cited

U.S. PATENT DOCUMENTS

| 5,144,006 | A | * | 9/1992 | Tam ............... 530/345 |
| 5,662,699 | A | | 9/1997 | Hamedi et al. |
| 5,789,542 | A | | 8/1998 | McLaughlin et al. |
| 6,068,829 | A | | 5/2000 | Ruoslahti et al. |
| 6,174,687 | B1 | | 1/2001 | Rajotte et al. |
| 6,180,084 | B1 | | 1/2001 | Ruoslahti et al. |
| 6,232,287 | B1 | * | 5/2001 | Ruoslahti et al. ............ 514/2 |
| 6,296,832 | B1 | | 10/2001 | Ruoslahti et al. |
| 6,303,573 | B1 | | 10/2001 | Ruoslahti et al. |
| 6,306,365 | B1 | | 10/2001 | Ruoslahti et al. |
| 6,491,894 | B1 | | 12/2002 | Ruoslahti et al. |
| 6,528,481 | B1 | | 3/2003 | Burg et al. |
| 6,610,651 | B1 | | 8/2003 | Ruoslahti et al. |
| 6,743,892 | B1 | | 6/2004 | Ruoslahti et al. |
| 6,784,153 | B1 | | 8/2004 | Rajotte et al. |
| 6,933,281 | B2 | | 8/2005 | Ruoslahti et al. |
| 7,018,615 | B2 | | 3/2006 | Ruoslahti et al. |
| 7,144,860 | B2 | | 12/2006 | Ruoslahti et al. |
| 7,192,921 | B2 | | 3/2007 | Laakkonen et al. |
| 2003/0055236 | A1 | * | 3/2003 | Moore et al. ............ 536/23.2 |
| 2005/0064507 | A1 | * | 3/2005 | Shaw ............... 435/7.1 |

FOREIGN PATENT DOCUMENTS

| WO | WO/97/10507 | 3/1997 |
| WO | WO/98/10795 | 3/1998 |
| WO | WO/99/46284 | 9/1999 |
| WO | WO/00/42973 | 7/2000 |
| WO | WO/00/48464 | 8/2000 |
| WO | WO/00/75174 | 12/2000 |
| WO | WO0168679 | * 9/2001 |

OTHER PUBLICATIONS

Schraa et al., J control release, vol. 83, p. 241-51, Oct. 4, 2002, abstract.*
Database A-Geneseq No. AAY36559.*
Database A-Geneseq No. ADU17039.*
Sequence search results (SEQ ID No. 5, 9, 15).*
Porkka et al., PNAS, vol. 99, p. 7444-7449, 200.*
Alvarez-Bravo et al., "Novel synthetic antimicrobial peptides effective against methicillin-resistant *Staphylococcus aureus*," *Biochem. J.* 302:535-538 (1994).
Arap et al., "Cancer treatment by targeted drug delivery to tumor vasculature in a mouse model," *Science* 279:377-380 (1998).
Bergers et al., "Angiogenesis and apoptosis are cellular parameters of neoplastic progression in transgenic mouse models of tumorigenesis," *Int. J. Dev. Biol.* 42:995-1002 (1998).
Bergers et al., "Benefits of targeting both pericytes and endothelial cells in the tumor vasculature with kinase inhibitors," *J. Clin. Invest.* 111:1287-1295 (2003).
Bergers et al., "Effects of angiogenesis inhibitors on multistage carcinogenesis in mice," *Science* 284:808-812 (1999).
Bergsten et al., "PDGF-D is a specific, protease-activated ligand for the PDGF beta-receptor," *Nat. Cell Biol.* 3:512-516 (2001).
Bessalle et al., "All-D-magainin: chirality, antimicrobial activity and proteolytic resistance," *FEBS Lett.* 274:151-155 (1990).
Blondelle and Houghten, "Design of model amphipathic peptides having potent antimicrobial activities," *Biochem.* 31:12688-12694 (1992).
Blondelle and Houghten, *Annual Reports in Medicinal Chemistry*, Academic Press, San Diego, 159-168, (1992).
Boehm et al., "Antiangiogenic therapy of experimental cancer does not induce acquired drug resistance," *Nature* 390:404-407 (1997).

(Continued)

*Primary Examiner*—Larry R. Helms
*Assistant Examiner*—Lei Yao
(74) *Attorney, Agent, or Firm*—McDermott Will & Emery LLP

(57) ABSTRACT

The invention provides a conjugate that includes a therapeutic moiety linked to a peptide or peptidomimetic that selectively homes to vasculature of premalignant pancreas. The peptide or peptidomimetic contains at least 5 contiguous amino acids of an amino acid sequence selected from CRSRKG (SEQ ID NO:9) and CEYQLDVE (SEQ ID NO:34), or a conservative variant or peptidomimetic thereof. The invention additionally provides a conjugate containing a therapeutic moiety linked to a peptide or peptidomimetic that selectively homes to pancreatic tumor cells and pancreatic tumor vasculature, the peptide or peptidomimetic comprising at least 5 contiguous amino acids of an amino acid sequence selected from CKAAKNK (SEQ ID NO:15), CKGAKAR (SEQ ID NO:19), and VGVGEWSV (SEQ ID NO:35), or a conservative variant or peptidomimetic thereof.

45 Claims, 9 Drawing Sheets

OTHER PUBLICATIONS

Bohme et al., "Primary structure of the long and short splice variants of mouse collagen XII and their tissue-specific expression during embryonic development," *Dev. Dyn.* 204:432-445 (1995).

Castronovo and Belotti, "TNP-470 (AGM-1470): mechanisms of action and early clinical development," *Eur. J. Cancer* 32A:2520-2527 (1996).

Chan et al., "Prospective randomized trial of docetaxel versus doxorubicin in patients with metastatic breast cancer," *J. Clin. Oncol.* 17:2341-2354 (1999).

Chaudhry et al., "Expression of platelet-derived growth factor and its receptors in neuroendocrine tumors of the digestive system," *Cancer Research*, 52:1006-1012 (1992).

Crown, "The platinum agents: a role in breast cancer treatment?" *Seminars in Oncol.* 28:28-37 (2001).

Efrat et al., "Beta-cell lines derived from transgenic mice expressing a hybrid insulin gene-oncogene," *Proc. Natl. Acad. Sci. USA* 85:9037-9041 (1988).

Folkman et al., "Induction of angiogenesis during the transition from hyperplasia to neoplasia," *Nature* 339:58-61 (1989).

Gohring et al., "Mapping of the binding of platelet-derived growth factor to distinct domains of the basement membrane proteins BM-40 and perlecan and distinction from the BM-40 collagen-binding epitope," *Eur. J. Biochem.* 255:60-66 (1998).

Griffith et al., Methionine aminopeptidase (type 2) is the common target for angiogenesis inhibitors AGM-1470 and ovalicin, *Chem Biol.* 4:461-471 (1997).

Hagedorn and Bikfalvi, "Target molecules for anti-angiogenic therapy: from basic research to clinical trials," *Crit. Rev. Oncol. Hematol.* 34:89-110 (2000).

Hanahan, "Heritable formation of pancreatic beta-cell tumours in transgenic mice expressing recombinant insulin/simian virus 40 oncogenes," *Nature* 315:115-122 (1985).

Hashizume et al, "Openings between defective endothelial cells explain tumor vessel leakiness," *Am. J. Pathol.* 156:1363-1380 (2000).

Homandberg et al., "Heparin-binding fragments of fibronectin are potent inhibitors of endothelial cell growth," *Am. J. Path.* 120:327-332 (1985).

Homandberg, et al., "Heparin-binding fragments of fibronectin are potent inhibitors of endothelial cell growth: structure-function correlations," *Biochim. Biophys. Acta* 874:61-71 (1986).

Ingber et al., "Synthetic analogues of fumagillin that inhibit angiogenesis and suppress tumour growth," *Nature* 348:555-557 (1990).

Javadpour et al., "De novo antimicrobial peptides with low mammalian cell toxicity," *J. Med. Chem.* 39:3107-3113 (1996).

Johnsson et al., "The c-sis gene encodes a precursor of the B chain of platelet-derived growth factor," *EMBO J.* 3:921-928 (1984).

Kirsch et al., "Anti-angiogenic treatment strategies for malignant brain tumors," *J. Neurooncol.* 50:149-163 (2000).

Laakkonen et al., "A tumor-homing peptide with a targeting specificity related to lymphatic vessels," *Nat. Med.* 8:751-755 (2002).

Larochelle et al., "PDGF-D, a new protease-activated growth factor," *Nat. Cell Biol.* 3:517-521 (2001).

Lopez and Hanahan, "Elevated levels of IGF-1 receptor convey invasive and metastatic capability in a mouse model of pancreatic islet tumorigenesis," *Cancer Cell* 1:339-353 (2002).

Maloy and Kari, "Structure-activity studies on magainins and other host defense peptides," *Biopolymers* 37:105-122 (1995).

Mancheno et al., "A peptide of nine amino acid residues from alpha-sarcin cytotoxin is a membrane-perturbing structure," *J. Peptide Res.* 51:142-148 (1998).

Morikawa et al., Abnormalities in pericytes on blood vessels and endothelial sprouts in tumors, *Am. J. Pathol.* 160:985-1000 (2002).

O'Reilly et al., "Angiostatin induces and sustains dormancy of human primary tumors in mice" *Nature Med.* 2:689-692 (1996).

O'Reilly et al., "Angiostatin: a novel angiogenesis inhibitor that mediates the suppression of metastases by a Lewis lung carcinoma," *Cell* 79:315-328 (1994).

O'Reilly et al., "Antiangiogenic activity of the cleaved conformation of the serpin antithrombin," *Science* 285:1926-1928 (1999).

O'Reilly et al., "Endostatin: an endogenous inhibitor of angiogenesis and tumor growth," *Cell* 88:277-285 (1997).

Oh et al., "Tissue-specific expression of type XII collagen during mouse embryonic development," *Dev. Dyn.* 196:37-46 (1993).

Parangi et al., "Tumor suppressor loci on mouse chromosomes 9 and 16 are lost at distinct stages of tumorigenesis in a transgenic model of islet cell carcinoma," *Cancer Res.* 55:6071-6076 (1995).

Paridaens et al., "Paclitaxel versus doxorubicin as first-line single-agent chemotherapy for metastatic breast cancer: a European Organization for Research and Treatment of Cancer Randomized Study with cross-over," *J. Clin. Oncol.* 18:724-733 (2000).

Pasqualini et al., "Aminopeptidase N is a receptor for tumor-homing peptides and a target for inhibiting angiogenesis," *Cancer Res.* 60:722-727 (2000).

Porkka et al., "A fragment of the HMGN2 protein homes to the nuclei of tumor cells and tumor endothelial cells in vivo," *Proc. Natl. Acad. Sci. USA* 99:7444-7449 (2002).

Rajotte et al., "Molecular heterogeneity of the vascular endothelium revealed by in vivo phage display," *J. Clin. Invest.* 102:430-437 (1998).

Sin et al., "The anti-angiogenic agent fumagillin covalently binds and inhibits the methionine aminopeptidase, MetAP-2," *Proc. Natl. Acad. Sci. U.S.A.* 94:6099-6103 (1997).

Somasundaram and Schuppan, "Type I, II, III, IV, V, and VI collagens serve as extracellular ligands for the isoforms of platelet-derived growth factor (AA, BB, and AB)," *J. Biol. Chem.* 271:26884-26891 (1996).

St. Croix et al., "Genes expressed in human tumor endothelium," *Science* 289:1197-1202 (2000).

Talbot and Brown, "Experimental and clinical studies on the use of matrix metalloproteinase inhibitors for the treatment of cancer," *Eur. J. Cancer* 32A:2528-2533 (1996).

Thurston et al., "Cationic liposomes target angiogenic endothelial cells in tumors and chronic inflammation in mice," *J. Clin. Invest.* 101:1401-1413 (1998).

Genbank Accession No. A85278 (Sequence 8 from Patent WO9840497).

Genbank Accession No. AAG38567 (C-mos [*Uta stansburiana*]).

Genbank Accession No. AAO15443 (AB14 [*Homo sapiens*]).

Genbank Accession No. AAO61967 (rp L15 [*Aster yellows phytoplasma*]).

Genbank Accession No. BAB47193 (hypothetical protein [*Escherichia coli* O157:H7]).

Genbank Accession No. BAC25606 (unnamed protein product [*Mus musculus*]).

Genbank Accession No. G72166 ((A26L protein—variola minor virus (strain Garcia-1996)).

Genbank Accession No. NP_076142 (wingless-related MMTV integration site 2 [*Mus musculus*]).

Genbank Accession No. NP_113961 (RNA polymerase 1-2; RNA polymerase I (127 kDa subunit) [*Rattus norvegicus*]).

Genbank Accession No. NP_486904 (probable glycosyl transferase [*Nostoc* sp. PCC 7120]).

Genbank Accession No. NP_509987 (putative secreted or extracellular protein precursor (19.5 kD) (XM503) [*Caenorhabditis elegans*]).

Genbank Accession No. NP_542376 (alpha 1 type XII collagen short isoform precursor [*Homo sapiens*]).

Genbank Accession No. NP_594310 (putative thioltransferase (glutaredoxin) [*Schizosaccharomyces pombe*]).

Genbank Accession No. NP_744592 (trascriptional regulator, LysR family [*Pseudomonas putida* KT2440]).

Genbank Accession No. NP_781370 (hypothetical protein CTC00704 [*Clostridium tetani* E88]).

Genbank Accession No. O35161 (Cadherin EGF LAG seven-pass G-type receptor 1 precursor).

Genbank Accession No. P16092 (Basic fibroblast growth factor receptor 1 precursor (FGFR-1) (bFGF-R) (MFR)).

Genbank Accession No. P31240 (platelet-derived growth factor, B chain precursor (PDGF B-chain) (PDGF-2) (c-sis)).

Genbank Accession No. Q06806 (Tyrosine-protein kinase receptor Tie-1 precursor).

Genbank Accession No. Q60847 (Collagen alpha 1 (XII) chain precursor).

Genbank Accession No. Q64151 (Semaphorin 4C precursor (Semaphorin I) (Sema I) (Semaphorin C-like 1) (M-Sema F)).

Genbank Accession No. Q9P246 (stromal interaction molecule 2 precursor).

Genbank Accession No. Q9Z0S7 (Claudin-9).

Genbank Accession No. S33551 (hypothetical protein 134—maize).

Genbank Accession No. S65712 (metallothionein 1—rat (fragments)).

Genbank Accession No. T03199 (hypothetical protein 73—rice mitochondrion).

Genbank Accession No. XP_161193 (hypothetical protein XP_161193 [Mus musculus]).

Genbank Accession No. ZP_0059494 (hypothetical protein [Thermobifida fusca]).

Genbank Accession No. ZP_00070671 (hypothetical protein [Oenococcus oeni MCW]).

Genbank Accession No. ZP_00087590 (COG0583: transcriptional regulator [Pseudomonas fluorescens PfO-1]).

* cited by examiner

SEQUENCE LISTING

```
<160> NUMBER OF SEQ ID NOS: 40

<210> SEQ ID NO 1
<211> LENGTH: 4
<212> TYPE: PRT
<213> ORGANISM: Artificial Sequence
<220> FEATURE:
<223> OTHER INFORMATION: synthetic peptide

<400> SEQUENCE: 1

Arg Gly Arg Arg
 1

<210> SEQ ID NO 2
<211> LENGTH: 5
<212> TYPE: PRT
<213> ORGANISM: Artificial Sequence
<220> FEATURE:
<223> OTHER INFORMATION: synthetic peptide

<400> SEQUENCE: 2

Arg Gly Arg Arg Ser
 1               5

<210> SEQ ID NO 3
<211> LENGTH: 6
<212> TYPE: PRT
<213> ORGANISM: Artificial Sequence
<220> FEATURE:
<223> OTHER INFORMATION: synthetic peptide

<400> SEQUENCE: 3

Arg Gly Arg Arg Ser Thr
 1               5

<210> SEQ ID NO 4
<211> LENGTH: 6
<212> TYPE: PRT
<213> ORGANISM: Artificial Sequence
<220> FEATURE:
<223> OTHER INFORMATION: synthetic peptide
```

```
<400> SEQUENCE: 4

Cys Arg Gly Arg Arg Ser
1               5

<210> SEQ ID NO 5
<211> LENGTH: 7
<212> TYPE: PRT
<213> ORGANISM: Artificial Sequence
<220> FEATURE:
<223> OTHER INFORMATION: synthetic peptide

<400> SEQUENCE: 5

Cys Arg Gly Arg Arg Ser Thr
1               5

<210> SEQ ID NO 6
<211> LENGTH: 5
<212> TYPE: PRT
<213> ORGANISM: Artificial Sequence
<220> FEATURE:
<223> OTHER INFORMATION: synthetic peptide
<220> FEATURE:
<221> NAME/KEY: VARIANT
<222> LOCATION: (1)...(5)
<223> OTHER INFORMATION: Xaa = Any  Basic Amino Acid

<400> SEQUENCE: 6

Arg Ser Arg Xaa Gly
1               5

<210> SEQ ID NO 7
<211> LENGTH: 6
<212> TYPE: PRT
<213> ORGANISM: Artificial Sequence
<220> FEATURE:
<223> OTHER INFORMATION: synthetic peptide
<220> FEATURE:
<221> NAME/KEY: VARIANT
<222> LOCATION: (1)...(6)
<223> OTHER INFORMATION: Xaa = Any Basic Amino Acid

<400> SEQUENCE: 7

Cys Arg Ser Arg Xaa Gly
1               5

<210> SEQ ID NO 8
<211> LENGTH: 5
<212> TYPE: PRT
<213> ORGANISM: Artificial Sequence
<220> FEATURE:
<223> OTHER INFORMATION: synthetic peptide

<400> SEQUENCE: 8

Arg Ser Arg Lys Gly
1               5

<210> SEQ ID NO 9
<211> LENGTH: 6
<212> TYPE: PRT
<213> ORGANISM: Artificial Sequence
<220> FEATURE:
<223> OTHER INFORMATION: synthetic peptide

<400> SEQUENCE: 9

Cys Arg Ser Arg Lys Gly
1               5
```

```
<210> SEQ ID NO 10
<211> LENGTH: 5
<212> TYPE: PRT
<213> ORGANISM: Artificial Sequence
<220> FEATURE:
<223> OTHER INFORMATION: synthetic peptide
<220> FEATURE:
<221> NAME/KEY: VARIANT
<222> LOCATION: (1)...(5)
<223> OTHER INFORMATION: Xaa = Any Basic Amino Acid

<400> SEQUENCE: 10

Cys Lys Ala Xaa Lys
1               5

<210> SEQ ID NO 11
<211> LENGTH: 6
<212> TYPE: PRT
<213> ORGANISM: Artificial Sequence
<220> FEATURE:
<223> OTHER INFORMATION: synthetic peptide
<220> FEATURE:
<221> NAME/KEY: VARIANT
<222> LOCATION: (1)...(6)
<223> OTHER INFORMATION: Xaa = Any Basic Amino Acid

<400> SEQUENCE: 11

Cys Lys Ala Xaa Lys Asn
1               5

<210> SEQ ID NO 12
<211> LENGTH: 5
<212> TYPE: PRT
<213> ORGANISM: Artificial Sequence
<220> FEATURE:
<223> OTHER INFORMATION: synthetic peptide

<400> SEQUENCE: 12

Cys Lys Ala Ala Lys
1               5

<210> SEQ ID NO 13
<211> LENGTH: 6
<212> TYPE: PRT
<213> ORGANISM: Artificial Sequence
<220> FEATURE:
<223> OTHER INFORMATION: synthetic peptide

<400> SEQUENCE: 13

Cys Lys Ala Ala Lys Asn
1               5

<210> SEQ ID NO 14
<211> LENGTH: 5
<212> TYPE: PRT
<213> ORGANISM: Artificial Sequence
<220> FEATURE:
<223> OTHER INFORMATION: synthetic peptide

<400> SEQUENCE: 14

Lys Ala Ala Lys Asn
1               5

<210> SEQ ID NO 15
<211> LENGTH: 7
<212> TYPE: PRT
<213> ORGANISM: Artificial Sequence
<220> FEATURE:
```

```
<223> OTHER INFORMATION: synthetic peptide

<400> SEQUENCE: 15

Cys Lys Ala Ala Lys Asn Lys
 1               5

<210> SEQ ID NO 16
<211> LENGTH: 4
<212> TYPE: PRT
<213> ORGANISM: Artificial Sequence
<220> FEATURE:
<223> OTHER INFORMATION: synthetic peptide

<400> SEQUENCE: 16

Ala Lys Ala Arg
 1

<210> SEQ ID NO 17
<211> LENGTH: 5
<212> TYPE: PRT
<213> ORGANISM: Artificial Sequence
<220> FEATURE:
<223> OTHER INFORMATION: synthetic peptide

<400> SEQUENCE: 17

Gly Ala Lys Ala Arg
 1               5

<210> SEQ ID NO 18
<211> LENGTH: 6
<212> TYPE: PRT
<213> ORGANISM: Artificial Sequence
<220> FEATURE:
<223> OTHER INFORMATION: synthetic peptide

<400> SEQUENCE: 18

Lys Gly Ala Lys Ala Arg
 1               5

<210> SEQ ID NO 19
<211> LENGTH: 7
<212> TYPE: PRT
<213> ORGANISM: Artificial Sequence
<220> FEATURE:
<223> OTHER INFORMATION: synthetic peptide

<400> SEQUENCE: 19

Cys Lys Gly Ala Lys Ala Arg
 1               5

<210> SEQ ID NO 20
<211> LENGTH: 6
<212> TYPE: PRT
<213> ORGANISM: Artificial Sequence
<220> FEATURE:
<223> OTHER INFORMATION: synthetic peptide

<400> SEQUENCE: 20

Cys Lys Gly Ala Lys Ala
 1               5

<210> SEQ ID NO 21
<211> LENGTH: 4
<212> TYPE: PRT
<213> ORGANISM: Artificial Sequence
<220> FEATURE:
<223> OTHER INFORMATION: synthetic peptide
```

```
<400> SEQUENCE: 21

Arg Val Gly Val
 1

<210> SEQ ID NO 22
<211> LENGTH: 5
<212> TYPE: PRT
<213> ORGANISM: Artificial Sequence
<220> FEATURE:
<223> OTHER INFORMATION: synthetic peptide

<400> SEQUENCE: 22

Arg Val Gly Val Ala
 1               5

<210> SEQ ID NO 23
<211> LENGTH: 6
<212> TYPE: PRT
<213> ORGANISM: Artificial Sequence
<220> FEATURE:
<223> OTHER INFORMATION: synthetic peptide

<400> SEQUENCE: 23

Arg Val Gly Val Ala Asp
 1               5

<210> SEQ ID NO 24
<211> LENGTH: 5
<212> TYPE: PRT
<213> ORGANISM: Artificial Sequence
<220> FEATURE:
<223> OTHER INFORMATION: synthetic peptide

<400> SEQUENCE: 24

Val Gly Val Ala Asp
 1               5

<210> SEQ ID NO 25
<211> LENGTH: 6
<212> TYPE: PRT
<213> ORGANISM: Artificial Sequence
<220> FEATURE:
<223> OTHER INFORMATION: synthetic peptide

<400> SEQUENCE: 25

Val Gly Val Ala Asp Val
 1               5

<210> SEQ ID NO 26
<211> LENGTH: 7
<212> TYPE: PRT
<213> ORGANISM: Artificial Sequence
<220> FEATURE:
<223> OTHER INFORMATION: synthetic peptide

<400> SEQUENCE: 26

Arg Val Gly Val Ala Asp Val
 1               5

<210> SEQ ID NO 27
<211> LENGTH: 8
<212> TYPE: PRT
<213> ORGANISM: Artificial Sequence
<220> FEATURE:
<223> OTHER INFORMATION: synthetic peptide
```

```
<400> SEQUENCE: 27

Phe Arg Val Gly Val Ala Asp Val
 1               5

<210> SEQ ID NO 28
<211> LENGTH: 5
<212> TYPE: PRT
<213> ORGANISM: Artificial Sequence
<220> FEATURE:
<223> OTHER INFORMATION: synthetic peptide

<400> SEQUENCE: 28

Cys Glu Tyr Gln Leu
 1               5

<210> SEQ ID NO 29
<211> LENGTH: 5
<212> TYPE: PRT
<213> ORGANISM: Artificial Sequence
<220> FEATURE:
<223> OTHER INFORMATION: synthetic peptide

<400> SEQUENCE: 29

Glu Tyr Gln Leu Asp
 1               5

<210> SEQ ID NO 30
<211> LENGTH: 6
<212> TYPE: PRT
<213> ORGANISM: Artificial Sequence
<220> FEATURE:
<223> OTHER INFORMATION: synthetic peptide

<400> SEQUENCE: 30

Glu Tyr Gln Leu Asp Val
 1               5

<210> SEQ ID NO 31
<211> LENGTH: 7
<212> TYPE: PRT
<213> ORGANISM: Artificial Sequence
<220> FEATURE:
<223> OTHER INFORMATION: synthetic peptide

<400> SEQUENCE: 31

Glu Tyr Gln Leu Asp Val Glu
 1               5

<210> SEQ ID NO 32
<211> LENGTH: 5
<212> TYPE: PRT
<213> ORGANISM: Artificial Sequence
<220> FEATURE:
<223> OTHER INFORMATION: synthetic peptide

<400> SEQUENCE: 32

Tyr Gln Leu Asp Val
 1               5

<210> SEQ ID NO 33
<211> LENGTH: 6
<212> TYPE: PRT
<213> ORGANISM: Artificial Sequence
<220> FEATURE:
<223> OTHER INFORMATION: synthetic peptide

<400> SEQUENCE: 33
```

```
Tyr Gln Leu Asp Val Glu
 1               5

<210> SEQ ID NO 34
<211> LENGTH: 8
<212> TYPE: PRT
<213> ORGANISM: Artificial Sequence
<220> FEATURE:
<223> OTHER INFORMATION: synthetic peptide

<400> SEQUENCE: 34

Cys Glu Tyr Gln Leu Asp Val Glu
 1               5

<210> SEQ ID NO 35
<211> LENGTH: 8
<212> TYPE: PRT
<213> ORGANISM: Artificial Sequence
<220> FEATURE:
<223> OTHER INFORMATION: synthetic peptide

<400> SEQUENCE: 35

Val Gly Val Gly Glu Trp Ser Val
 1               5

<210> SEQ ID NO 36
<211> LENGTH: 4
<212> TYPE: PRT
<213> ORGANISM: Artificial Sequence
<220> FEATURE:
<223> OTHER INFORMATION: synthetic peptide

<400> SEQUENCE: 36

Val Gly Val Gly
 1

<210> SEQ ID NO 37
<211> LENGTH: 5
<212> TYPE: PRT
<213> ORGANISM: Artificial Sequence
<220> FEATURE:
<223> OTHER INFORMATION: synthetic peptide

<400> SEQUENCE: 37

Val Gly Val Gly Glu
 1               5

<210> SEQ ID NO 38
<211> LENGTH: 6
<212> TYPE: PRT
<213> ORGANISM: Artificial Sequence
<220> FEATURE:
<223> OTHER INFORMATION: synthetic peptide
<220> FEATURE:
<221> NAME/KEY: VARIANT
<222> LOCATION: (1)...(6)
<223> OTHER INFORMATION: Xaa = Any Amino Acid

<400> SEQUENCE: 38

Cys Arg Ser Arg Xaa Gly
 1               5

<210> SEQ ID NO 39
<211> LENGTH: 5
<212> TYPE: PRT
<213> ORGANISM: Artificial Sequence
<220> FEATURE:
```

```
-continued

<223> OTHER INFORMATION: synthetic peptide
<220> FEATURE:
<221> NAME/KEY: VARIANT
<222> LOCATION: (1)...(5)
<223> OTHER INFORMATION: Xaa = Any Amino Acid

<400> SEQUENCE: 39

Cys Lys Ala Xaa Lys
 1               5

<210> SEQ ID NO 40
<211> LENGTH: 8
<212> TYPE: PRT
<213> ORGANISM: Artificial Sequence
<220> FEATURE:
<223> OTHER INFORMATION: synthetic peptide
<220> FEATURE:
<221> NAME/KEY: VARIANT
<222> LOCATION: (1)...(8)
<223> OTHER INFORMATION: Xaa = Any Amino Acid

<400> SEQUENCE: 40

Phe Xaa Val Gly Val Ala Asp Val
 1               5
```

MOLECULES THAT SELECTIVELY HOME TO VASCULATURE OF PREMALIGNANT OR MALIGNANT LESIONS OF THE PANCREAS AND OTHER ORGANS

This application claims benefit of provisional application Ser. No. 60/516,118, filed Oct. 31, 2003, which is herein incorporated by reference.

This invention was made with government support under CA82713, awarded by the National Cancer Institute, and DAMD 17-02-1-0315, awarded by the Department of Defense. The government has certain rights in this invention.

BACKGROUND OF THE INVENTION

1. Field of the Invention

A hurdle to advances in preventing and treating cancer is the lack of agents that effectively target a cancer or precancerous tissue while sparing normal tissues. Radiation therapy and surgery, which are typically localized treatments, can cause substantial damage to normal tissue in the treatment field, resulting in scarring and loss of normal tissue. Furthermore, chemotherapy, which is typically a systemic treatment, can cause substantial damage to normal organs such as non-cancerous skin, bone marrow, mucosa, and small intestine, in particular because these tissues undergo rapid cell turnover and continuous cell division. As a result, undesirable side effects such as nausea, loss of hair and drop in blood cell count can result from systemic treatment with a chemotherapeutic agent. Such undesirable side effects often limit the amount of drug that can be safely administered, thereby reducing patient survival rates and quality of life.

Selective delivery of therapeutics such as anti-angiogenic agents to vasculature that supports tumors would result in less toxic therapy since rapidly proliferating normal cells would be spared. Similarly, selective delivery of anti-angiogenic agents to vasculature of premalignant tissues would provide a prophylactic strategy for reducing the risk of cancer. However, to date, it has been difficult to produce drugs that are delivered specifically to tumor vasculature or to vasculature of premalignant tissues. Thus, there is a need for molecules that selectively target tumor tissues and vasculature, such as pancreatic tumors and vasculature, as well as for molecules that selectively target premalignant tissues and vasculature, such as premalignant pancreas and vasculature. The present invention satisfies these needs and provides related advantages as well.

2. Background Information

A hurdle to advances in preventing and treating cancer is the lack of agents that effectively target a cancer or precancerous tissue while sparing normal tissues. Radiation therapy and surgery, which are typically localized treatments, can cause substantial damage to normal tissue in the treatment field, resulting in scarring and loss of normal tissue. Furthermore, chemotherapy, which is typically a systemic treatment, can cause substantial damage to normal organs such as non-cancerous skin, bone marrow, mucosa, and small intestine, in particular because these tissues undergo rapid cell turnover and continuous cell division. As a result, undesirable side effects such as nausea, loss of hair and drop in blood cell count can result from systemic treatment with a chemotherapeutic agent. Such undesirable side effects often limit the amount of drug that can be safely administered, thereby reducing patient survival rates and quality of life.

Selective delivery of therapeutics such as anti-angiogenic agents to vasculature that supports tumors would result in less toxic therapy since rapidly proliferating normal cells would be spared. Similarly, selective delivery of anti-angiogenic agents to vasculature of premalignant tissues would provide a prophylactic strategy for reducing the risk of cancer. However, to date, it has been difficult to produce drugs that are delivered specifically to tumor vasculature or to vasculature of premalignant tissues. Thus, there is a need for molecules that selectively target tumor tissues and vasculature, such as pancreatic tumors and vasculature, as well as for molecules that selectively target premalignant tissues and vasculature, such as premalignant pancreas and vasculature. The present invention satisfies these needs and provides related advantages as well.

SUMMARY OF THE INVENTION

The invention provides a peptide or peptidomimetic having a length of less than 60 amino acid residues and containing at least 5 contiguous amino acids of CRGRRST (SEQ ID NO:5), CRSRKG (SEQ ID NO:9), CKAAKNK (SEQ ID NO:15), CKGAKAR (SEQ ID NO:19), FRVGVADV (SEQ ID NO:27), CEYQLDVE (SEQ ID NO:34) and VGVGEWSV (SEQ ID NO:35), or a conservative variant or peptidomimetic thereof. In embodiments of the invention, the peptide or peptidomimetic contains 40 amino acids, 20 amino acids or 10 amino acids.

The invention provides a conjugate that includes a therapeutic moiety linked to a peptide or peptidomimetic that selectively homes to vasculature of premalignant pancreas. The peptide or peptidomimetic contains at least 5 contiguous amino acids of an amino acid sequence selected from CRSRKG (SEQ ID NO:9) and CEYQLDVE (SEQ ID NO:34), or a conservative variant or peptidomimetic thereof. In embodiments of the invention, the peptide or peptidomimetic has a length of less than 100 residues, less than 50 residues and less than 25 residues. Also provided by the invention is a conjugate containing a therapeutic moiety linked to a peptide or peptidomimetic that selectively homes to vasculature of premalignant pancreas, in which the peptide or peptidomimetic binds specifically to a cognate receptor for SEQ ID NO:9 or SEQ ID NO:34.

The invention additionally provides a conjugate containing a therapeutic moiety linked to a peptide or peptidomimetic that selectively homes to pancreatic tumor cells and pancreatic tumor vasculature, the peptide or peptidomimetic comprising at least 5 contiguous amino acids of an amino acid sequence selected from CKAAKNK (SEQ ID NO:15), CKGAKAR (SEQ ID NO:19), and VGVGEWSV (SEQ ID NO:35), or a conservative variant or peptidomimetic thereof. In embodiments of the invention, the peptide or peptidomimetic has a length of less than 100 residues, less than 50 residues and less than 25 residues. Also provided by the invention is a conjugate that contains therapeutic moiety linked to a peptide or peptidomimetic that selectively homes to pancreatic tumor cells and pancreatic tumor vasculature, wherein the peptide or peptidomimetic binds specifically to a cognate receptor for SEQ ID NO:15, SEQ ID NO:19 or SEQ ID NO:35.

The invention provides a conjugate that contains a therapeutic moiety linked to a peptide or peptidomimetic that selectively homes to premalignant and malignant pancreatic vasculature, the peptide or peptidomimetic containing at least 5 contiguous amino acids of an amino acid sequence selected from CRGRRST (SEQ ID NO:5) and FRVGVADV (SEQ ID NO:27), or a conservative variant or peptidomimetic thereof. In embodiments of the invention, the peptide or peptidomimetic has a length of less than 100 residues, 50 residues and less than 25 residues. Also provided by the invention is a conjugate that contains a therapeutic moiety linked to a peptide or peptidomimetic that selectively homes to pancreatic tumor cells and pancreatic tumor vasculature, wherein the peptide or peptidomimetic binds specifically to a cognate receptor for SEQ ID NO:5 or SEQ ID NO:27

The conjugates of the invention can be linked to a variety of moieties. In one embodiment, the moiety is a therapeutic moiety. In another embodiment, the moiety is a detectable moiety.

The invention provides a multivalent conjugate, containing a therapeutic moiety linked to at least two peptides or peptidomimetics that selectively home to vasculature of premalignant pancreas, each of the peptides or peptidomimetics containing at least 5 contiguous amino acids of an amino acid sequence selected from CRSRKG (SEQ ID NO:9) and CEYQLDVE (SEQ ID NO:34).

The invention also provides a multivalent conjugate that contains a therapeutic moiety linked to at least two peptides or peptidomimetics that selectively home to vasculature of premalignant pancreas, wherein each of the peptides or peptidomimetics binds specifically to a cognate receptor for SEQ ID NO:9 or SEQ ID NO:34.

The invention further provides a multivalent conjugate that contains a therapeutic moiety linked to at least two peptides or peptidomimetics that selectively home to pancreatic tumor cells and pancreatic tumor vasculature, each of the peptides or peptidomimetics containing at least 5 contiguous amino acids of an amino acid sequence selected from CKAAKNK (SEQ ID NO:15), CKGAKAR (SEQ ID NO:19), and VGVGEWSV (SEQ ID NO:35), or a conservative variant or peptidomimetic thereof.

Also provided by the invention is a multivalent conjugate that contains a therapeutic moiety linked to at least two peptides or peptidomimetics that selectively home to premalignant and malignant pancreatic vasculature, wherein each of the peptides or peptidomimetics binds specifically to a cognate receptor for an amino acid sequence selected from CKAAKNK (SEQ ID NO:15), CKGAKAR (SEQ ID NO:19), and VGVGEWSV (SEQ ID NO:35).

The invention provides a multivalent conjugate that contains a therapeutic moiety linked to at least two peptides or peptidomimetics that selectively home to premalignant and malignant vasculature, each of the peptides or peptidomimetics containing at least 5 contiguous amino acids of an amino acid sequence selected from CRGRRST (SEQ ID NO:5) and FRVGVADV (SEQ ID NO:27), or a conservative variant or peptidomimetic thereof.

Also provided is a multivalent conjugate that contains a therapeutic moiety linked to at least two peptides or peptidomimetics that selectively home to pancreatic tumor cells and pancreatic tumor vasculature, wherein each of the peptides or peptidomimetics binds specifically to a cognate receptor for an amino acid sequence selected from CRGRRST (SEQ ID NO:5) and FRVGVADV (SEQ ID NO:27).

The invention provides a method of directing a moiety to a pancreatic premalignant lesion in an individual. The method involves administering to the individual a conjugate containing a moiety linked to (a) a peptide or peptidomimetic that selectively homes to vasculature of premalignant pancreas, the peptide or peptidomimetic containing at least 5 contiguous amino acids of an amino acid sequence selected from CRSRKG (SEQ ID NO:9) and CEYQLDVE (SEQ ID NO:34), or a conservative variant or peptidomimetic thereof, or (b) a peptide or peptidomimetic that selectively homes to premalignant and malignant pancreatic vasculature, the peptide or peptidomimetic containing at least 5 contiguous amino acids of an amino acid sequence selected from CRGRRST (SEQ ID NO:5) and FRVGVADV (SEQ ID NO:27), or a conservative variant or peptidomimetic thereof, thereby directing the moiety to the vasculature of the pancreatic premalignant lesion. In one embodiment, the moiety is a therapeutic moiety, such as an angiogenic inhibitor. In another embodiment, the moiety is a diagnostic moiety.

The invention provides a method of imaging pancreatic premalignant lesions in an individual. The method involves: (a) administering to the individual a conjugate containing a detectable moiety linked to a peptide or peptidomimetic that selectively homes to vasculature of premalignant pancreas, the peptide or peptidomimetic containing at least 5 contiguous amino acids of an amino acid sequence selected from CRSRKG (SEQ ID NO:9) and CEYQLDVE (SEQ ID NO:34), or a conservative variant or peptidomimetic thereof, and (b) detecting the conjugate, thereby imaging pancreatic premalignant lesions.

Further provided by the invention is a method of treating a pancreatic premalignant lesion in an individual. The method involves administering to the individual a conjugate containing a therapeutic moiety linked to: (a) a peptide or peptidomimetic that selectively homes to premalignant and malignant pancreatic vasculature, the peptide or peptidomimetic containing at least 5 contiguous amino acids of an amino acid sequence selected from CRGRRST (SEQ ID NO:5), and FRVGVADV (SEQ ID NO:27), or a conservative variant or peptidomimetic thereof, or (b) a peptide or peptidomimetic that selectively homes to vasculature of premalignant pancreas containing at least 5 contiguous amino acids of an amino acid sequence selected from CRSRKG (SEQ ID NO:9) and CEYQLDVE (SEQ ID NO:34), thereby directing the therapeutic moiety to the pancreatic premalignant lesion in the individual to treat the pancreatic premalignant lesion. In one embodiment, the moiety is a therapeutic moiety, such as an angiogenic inhibitor.

The invention provides of directing a moiety to pancreatic tumor cells and pancreatic tumor vasculature in an individual. The method involves administering to the individual a conjugate containing a moiety linked to: (a) a peptide or peptidomimetic that selectively homes to pancreatic tumor cells and pancreatic tumor vasculature, the peptide or peptidomimetic containing at least 5 contiguous amino acids of an amino acid sequence selected from CKAAKNK (SEQ ID NO:15), CKGAKAR (SEQ ID NO:19), FRVGVADV and VGVGEWSV (SEQ ID NO:35), or a conservative variant or peptidomimetic thereof, or (b) a peptide or peptidomimetic that selectively homes to premalignant and malignant pancreatic vasculature, the peptide or peptidomimetic containing at least 5 contiguous amino acids of an amino acid sequence selected from CRGRRST (SEQ ID NO:5) and FRVGVADV (SEQ ID NO:27), or a conservative variant or peptidomimetic thereof, thereby directing the moiety to pancreatic tumor cells and pancreatic tumor vasculature.

The invention provides a method of imaging pancreatic tumors and pancreatic tumor vasculature in an individual. The method involves (a) administering to the individual a conjugate containing a detectable moiety linked to a peptide or peptidomimetic that selectively homes to pancreatic tumor cells and pancreatic tumor vasculature, the peptide or peptidomimetic containing at least 5 contiguous amino acids of an amino acid sequence selected from CKAAKNK (SEQ ID NO:15), CKGAKAR (SEQ ID NO:19) and VGVGEWSV (SEQ ID NO:35), or a conservative variant or peptidomimetic thereof, and (b) detecting the conjugate, thereby imaging the pancreatic tumors and pancreatic tumor vasculature.

The invention provides a method of reducing the severity of pancreatic cancer in an individual. The method involves administering to the individual a conjugate containing a therapeutic moiety linked to: (a) a peptide or peptidomimetic that selectively homes to pancreatic tumor cells and pancreatic tumor vasculature, the peptide or peptidomimetic containing at least 5 contiguous amino acids of an amino acid sequence selected from CKAAKNK (SEQ ID NO:15), CKGAKAR (SEQ ID NO:19), FRVGVADV (SEQ ID NO:27) and VGVGEWSV (SEQ ID NO:35), or a conservative variant or peptidomimetic thereof, or (b) a peptide or peptidomimetic that selectively homes to premalignant and malignant pancreatic vasculature, the peptide or peptidomimetic containing at least 5 contiguous amino acids of an amino acid sequence selected from CRGRRST (SEQ ID NO:5) and FRVGVADV (SEQ ID NO:27), or a conservative variant or peptidomimetic thereof, thereby directing the therapeutic moiety to pancreatic tumor cells or pancreatic tumor vasculature in the individual to reduce the severity of the pancreatic cancer.

The invention provides a method of staging tumor progression in an individual having or suspected of having a pancreatic premalignant lesion or pancreatic tumor. The method involves: (a) administering to the individual at least one conjugate containing a detectable moiety linked to (i) a peptide or peptidomimetic that selectively homes to vasculature of premalignant pancreas, the peptide or peptidomimetic specifically binding a cognate receptor for CRSRKG (SEQ ID NO:9) or CEYQLDVE (SEQ ID NO:34), or (ii) a peptide or peptidomimetic that selectively homes to pancreatic tumor cells and pancreatic tumor vasculature, the peptide or peptidomimetic specifically binding a cognate receptor for an amino acid sequence selected from CKAAKNK (SEQ ID NO:15), CKGAKAR (SEQ ID NO:19) and VGVGEWSV (SEQ ID NO:35); and (b) detecting the conjugate, wherein detection of the conjugate containing a peptide or peptidomimetic that selectively homes to vasculature of premalignant pancreas indicates a premalignant stage of tumor progression in the individual and wherein detection of the conjugate containing a peptide or peptidomimetic that selectively homes to pancreatic tumor cells and pancreatic tumor vasculature indicates a malignant stage of tumor progression in the individual.

DETAILED DESCRIPTION OF THE INVENTION

The present invention is directed to the discovery of homing molecules that selectively home to vasculature of premalignant tissues and further directed to molecules that selectively home to tumor cells and tumor vasculature, such as premalignant pancreatic tissue and pancreatic tumor cells and tumor vasculature. As disclosed herein in Example I, peptides specific for premalignant pancreatic lesions or for pancreatic tumor cells and pancreatic tumor vasculature were isolated using a combination of in vivo and ex vivo selections using 12 week old RIP1-Tag2 mice.

The RIP1-Tag2 transgenic mouse is a prototypical mouse model of multistage tumorigenesis of islet cell carcinoma (Hanahan, *Nature* 315:115-122 (1985)). RIP1-Tag2 transgenic mice express the SV40 T antigens (Tag) under the control of the insulin gene promoter, which elicits the sequential development of tumors in the islets of Langerhans over a period of 12-14 weeks. Hyperplastic islets begin to appear at around 4 weeks of age, and angiogenesis is activated a few weeks later in a subset of the hyperplastic islets, producing angiogenic (dysplastic) islets (Bergers et al., *Int. J. Dev. Biol.* 42:995-1002 (1998); Folkman et al., *Nature* 339:58-61 (1989)). Solid tumors form beginning at 9-10 weeks, initially presenting as small nodules that grow and progress to large islet tumors with well defined margins as well as two classes of invasive carcinoma (Lopez and Hanahan, *Cell* 1:339-353 (2002)). As is described in Examples I and II, stage-specific molecular markers accessible via the circulation were identified, either on the surface of endothelial cells, their peri-endothelial support cells (pericytes and smooth muscle cells) or even tumor cells themselves (as a result of the hemorrhagic, leaky angiogenic vasculature). Phage pools that homed preferentially to different stages during RIP1-Tag2 tumorigenesis were identified using ex vivo and in vitro selections, as described in Examples I and II. Also identified were 'pan-angiogenic' markers shared by many types of tumors (Example IV).

Figure 1:
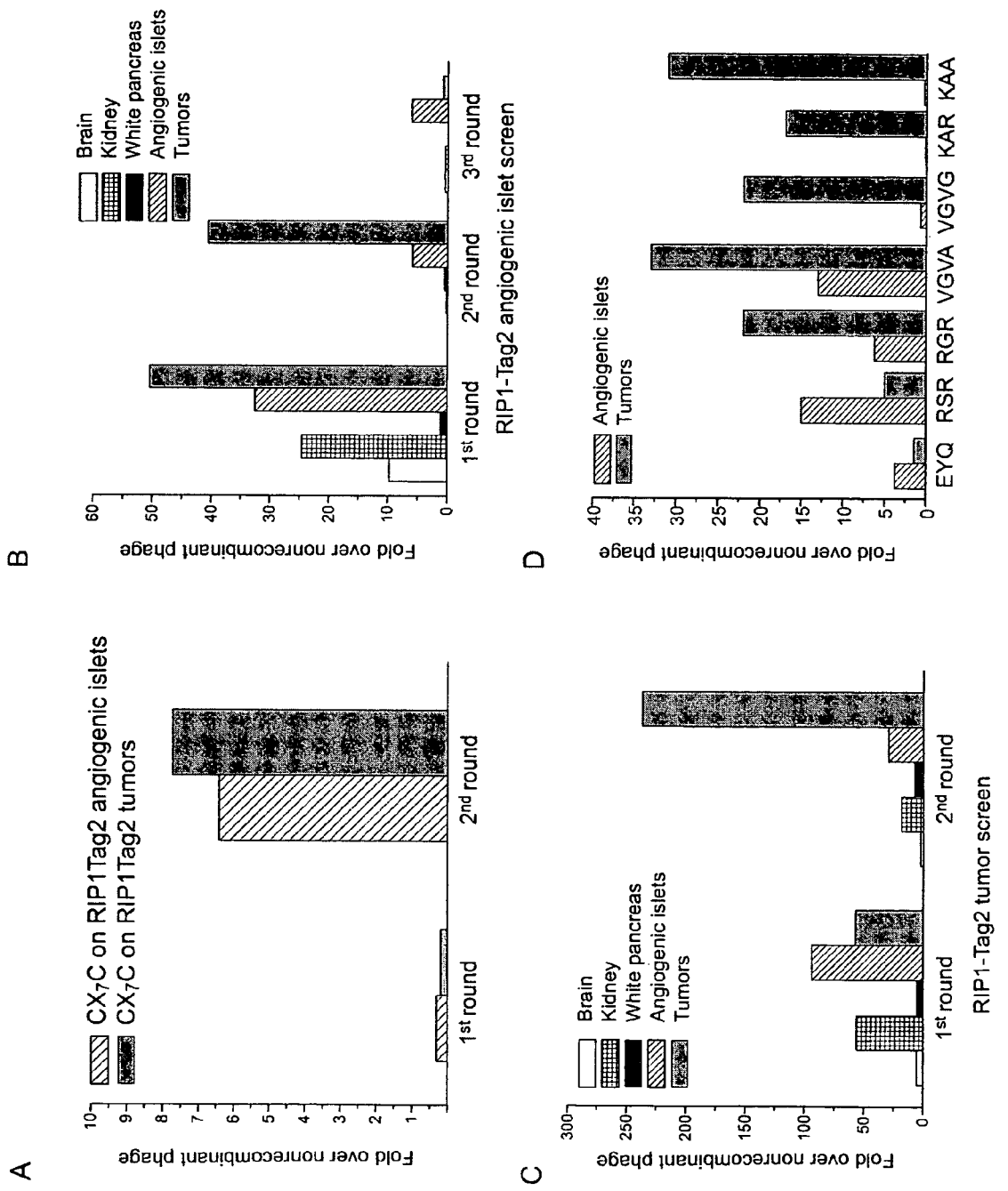
FIG. 1 shows that phage-displayed peptides selectively home to premalignant pancreas or pancreatic tumor cells. (A) Ex vivo screening on angiogenic islets or tumors derived from RIP1-Tag2 mice using the $CX_7C$ peptide library displayed on T7 phage. The enriched phage pools were used for subsequent in vivo homing in RIP1-Tag2 mice; (B) angiogenic islets (3 rounds of selection); (C) tumors (2 rounds of selection); (D) In vivo homing of individual phage to RIP1-Tag2 angiogenic islets and tumors.

Ex vivo selections were performed using suspensions of either angiogenic islets or solid tumors, and resulted in a 7 or 8-fold enrichment of phage relative to enrichment of nonrecombinant phage lacking displayed peptides, respectively (FIG. 1A). Sequential in vivo selection using angiogenic islets resulted in a 7-fold enrichment (FIG. 1B); and sequential in vivo using solid tumors resulted in an 8-fold enrichment (FIG. 1C). Peptides displayed on several of the selected phage clones were found to be highly selective for either angiogenic islets in comparison to solid tumors, or for solid tumors in comparison to angiogenic islets (FIG. 1D).

Sequencing of phage from the selected pools identified a number of peptide sequences that were represented more than once, and these were tested for their ability to bind cell suspensions prepared from angiogenic islets and tumors. Six of the phage selected for further analysis were from the tumor screen (referred to as KAA, RGR, RSR, VGVA, VGVG and KAR), and one (EYQ) was picked from the angiogenic screen. Peptide sequences corresponding to each of these peptide motifs are set forth as SEQ ID NO:15 (CKAAKNK), SEQ ID NO:5 (CRGRRST), SEQ ID NO:9 (CRSRKG), SEQ ID NO:27 (FRVGVADV), SEQ ID NO:35 (VGVGEWSV), SEQ ID NO:19 (CKGAKAR) and SEQ ID NO:34 (C EYQLDVE), respectively.

Each of the identified peptides was linear, although the phage library used ($CX_7C$) was designed to express primarily cyclized peptides, with a minority of linear peptides. However, linear peptides form in this library, for example, by the occurrence of a stop codon in a random insert, causing truncation of the peptide, and by occurrence of a frameshift mutation that mutates the second cysteine (which is required for cyclization) into valine.

To confirm homing specificity of the selected peptides, purified peptides were intravenously injected into 8-week or 12-week old RIP-Tag2 mice to examine peptide localization at early (angiogenic) or late (malignant) stages of tumor progression, respectively. The observed peptide localization profiles in each case was similar to those of cognate phage. As is described in Example IV, the peptides were found to be highly selective for premalignant angiogenic islets (RSR and EYQ peptides), malignant solid tumors (KAA and KAR peptides), or both angiogenic islets and tumors (RGR and VGVA peptides), and did not appreciably home to normal islets, kidney, brain, liver, lung or spleen.

To further characterize homing selectivity, tissues were collected following i.v. infusion with fluorescein-conjugated RSR, KAA, RGR peptides, sectioned, and evaluated with endothelial cell and endothelial lumen markers and a neovascular pericyte marker. All three peptides (RSR, KAA, and RGR) co-localized both with the endothelial cell and pericyte markers, indicating that each homes to and binds a moiety associated with both cell types (see, for example, FIG. 3). Co-localiztion of these peptides with the same markers in adjacent exocrine pancreas or in normal pancreatic islets was not observed.

Figure 4:
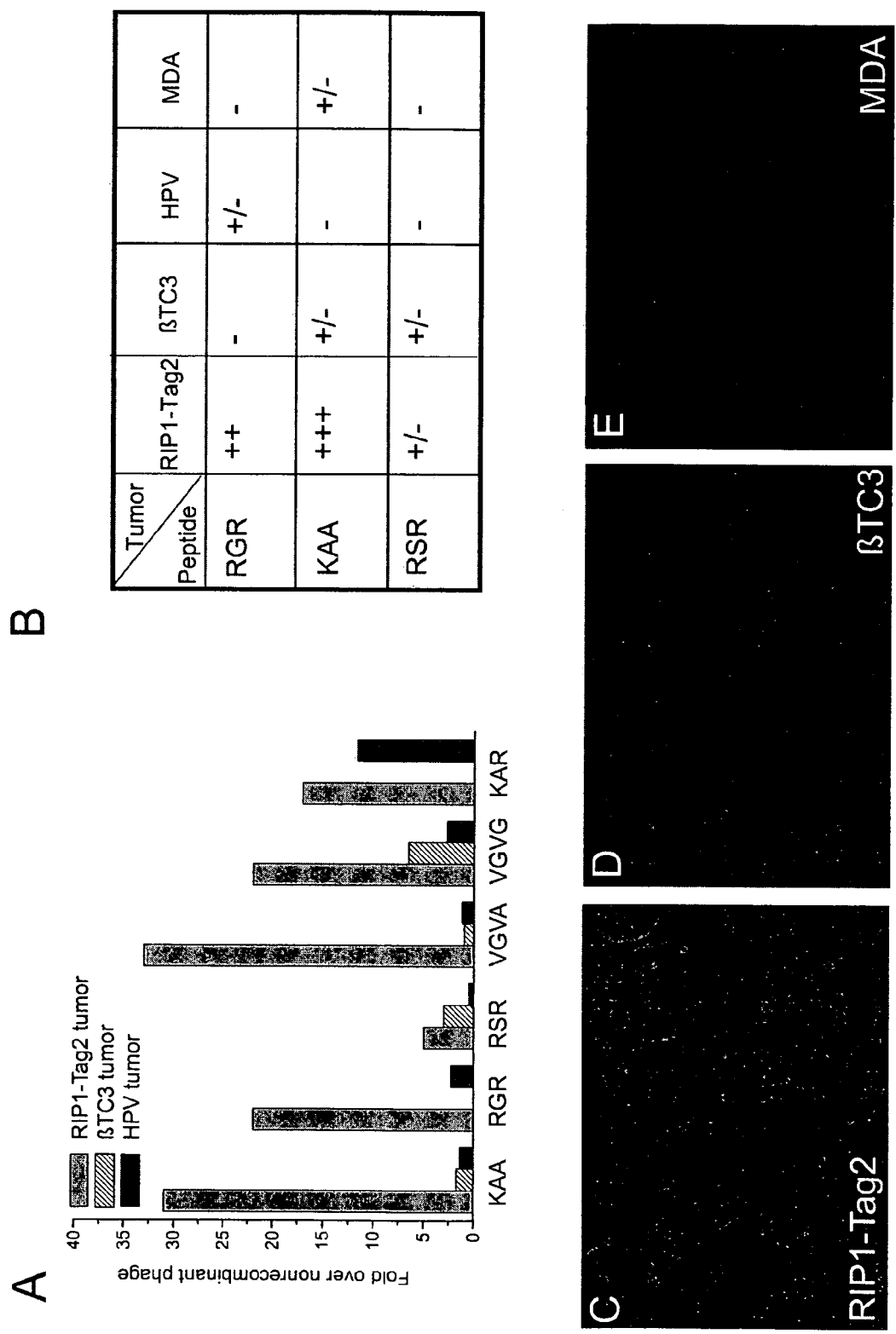
FIG. 4 shows evaluation of the specificity of selected homing phage and peptides. (A) Bar graph showing homing efficiency of individual phage to a pancreatic islet tumor in a RIP1-Tag2 mouse, a bTC3-derived subcutaneous transplant tumor in a nude mouse, and a squamous cell carcinoma in a K14-HPV16 mouse. (B) Table summarizing the relative homing of fluorescein-conjugated peptides to different tumor models; +++ indicates strong homing, as revealed by the fluorescent intensity of i.v. injected peptide, ++ indicates moderate homing, + indicates weak homing, − indicates absence of homing. Representative images of fluorescein-conjugated KAR peptide homing to a RIP1-Tag2 pancreatic islet tumor (C), a bTC3 subcutaneous tumor (D), and an MDA subcutaneous tumor (E) are also shown. Magnification shown is 200×.

As further disclosed in Example IV, homing selectivity of premalignant and/or malignant tissue peptides RGR, KAA, RSR, VGVA, VGVG, and KAR was analyzed for the ability of these peptides to home to endothelium in tumors of different tissue origins and localized to different anatomical locations. In particular, two subcutaneously implanted tumors and a tumor produced in a transgenic animal model were examined for accumulation of fluorescein-labeled peptides following intravenous injection. As shown in FIG. 4A, different homing specificities were observed for each peptide in the various tumor microenvironments. In particular, as shown in FIG. 4A, peptides KAA, RGR, RSR, VGVA, and VGVG did not home appreciably to HPV tumor, whereas peptide KAR homed to this tumor type. In addition, peptides KAA, RGR, VGVA, and KAR did not home appreciably to TC3 tumor, whereas peptides RSR and VGVG homed to this tumor type. As shown in FIG. 4B, peptides RGR and RSR did not home appreciably to MDA tumor, whereas peptide KAA homed to this tumor type.

As further disclosed in Example V, a receptor for the peptide RGR was identified using a combination of sequence searching and cell biological methods. Specifically, using sequence searching methods, a ligand for PDGFR-β was identified to contain the sequence RGRRS (SEQ ID NO:2). Using cell biological methods, phage containing the RGR sequence (CRGRRST; SEQ ID NO:5) was shown to bind to PDGFR-β expressing cells, but not to cells expressing a similar receptor (VSGFR2) or to control cells. The association of the CRGRRST (SEQ ID NO:5) peptide with PDGFRβ was confirmed when intravenously injected fluorescein-conjugated CRGRRST (SEQ ID NO:5) peptide was shown to co-localize with PDGFRβ, as visualized by subsequent immunostaining of tissue sections from RIP1-Tag2 tumors.

Peptides and Peptidomimetics

Based on the above findings, the present invention provides several isolated peptides and peptidomimetics that home to vasculature of premalignant pancreas, to pancreatic tumor cells and pancreatic tumor vasculature or to both premalignant and/or malignant pancreatic vasculature. In an embodiment, the invention provides an isolated peptide or peptidomimetic that selectively homes to vasculature of premalignant pancreas. The peptide contains at least 4 contiguous amino acids of the amino acid sequence CRSRKG (SEQ ID NO:9) or CEYQLDVE (SEQ ID NO:34), or a conservative variant or peptidomimetic thereof and has a length of less than 50 residues, such as less than 40 residues, less than 30 residues, less than 20 residues, less than 10 residues, or less than 8 residues.

In one embodiment, a peptide of the invention, as well as a peptide contained in a conjugate of the invention, contains at least 4 contiguous amino acids of the amino acid sequence CRSRKG (SEQ ID NO:9), or a conservative variant of peptidomimetic thereof. The peptide also can contain at least 5 contiguous amino acids of the amino acid sequence CRSRKG (SEQ ID NO:9), or at least 6 contiguous amino acids of the amino acid sequence CRSRKG (SEQ ID NO:9), or a conservative variant of peptidomimetic thereof. Exemplary peptide sequences that contain at least 4 contiguous amino acids of the amino acid sequence CRSRKG (SEQ ID NO:9) include, but are not limited to, $RSRX_1G$ wherein $X_1$ is a basic amino acid (SEQ ID NO:6), $CRSRX_1G$ wherein $X_1$ is a basic amino acid (SEQ ID NO:7), and RSRKG (SEQ ID NO:8). $X_1$ can be, for example, arginine, histidine and lysine.

In another embodiment, a peptide of the invention, as well as a peptide contained in a conjugate of the invention, contains at least 4 contiguous amino acids of the amino acid sequence CEYQLDVE (SEQ ID NO:34), or a conservative variant of peptidomimetic thereof. The peptide also can contain at least 5 contiguous amino acids of the amino acid sequence CEYQLDVE (SEQ ID NO:34), at least 6 contiguous amino acids of the amino acid sequence CEYQLDVE (SEQ ID NO:34), at least 7 contiguous amino acids of the amino acid sequence CEYQLDVE (SEQ ID NO:34), or at least 8 contiguous amino acids of the amino acid sequence CEYQLDVE (SEQ ID NO:34) or a conservative variant of peptidomimetic thereof. Exemplary peptide sequences that contain at least 4 contiguous amino acids of the amino acid sequence CEYQLDVE (SEQ ID NO:34) include, but are not limited to CEYQL (SEQ ID NO:28), EYQLD (SEQ ID NO:29), EYQLDV (SEQ ID NO:30), EYQLDVE (SEQ ID NO:31), YQLDV (SEQ ID NO:32), and YQLDVE (SEQ ID NO:33).

The invention also provides an isolated peptide or peptidomimetic that selectively homes to pancreatic tumor cells and pancreatic tumor vasculature. The peptide contains at least 4 contiguous amino acids of the amino acid sequence CKAAKNK (SEQ ID NO:15), CKGAKAR (SEQ ID NO:19) or VGVGEWSV (SEQ ID NO:35), or a conservative variant or peptidomimetic thereof and has a length of less than 50 residues, such as less than 40 residues, less than 30 residues, less than 20 residues, less than 10 residues, and less than 8 residues.

In one embodiment, a peptide of the invention, as well as a peptide contained in a conjugate of the invention, contains at least 4 contiguous amino acids of the amino acid sequence CKAAKNK (SEQ ID NO:15), or a conservative variant of peptidomimetic thereof. The peptide also can contain at least 5 contiguous amino acids of the amino acid sequence CKAAKNK (SEQ ID NO:15), at least 6 contiguous amino acids of the amino acid sequence CKAAKNK (SEQ ID NO:15), at least 7 contiguous amino acids of the amino acid sequence CKAAKNK (SEQ ID NO:15), or a conservative variant of peptidomimetic thereof. Exemplary peptide sequences that contain at least 4 contiguous amino acids of the amino acid sequence CKAAKNK (SEQ ID NO:15) include, but are not limited to CKAX$_1$K wherein X$_1$ is a basic amino acid (SEQ ID NO:10), CKAX$_1$KN wherein X$_1$ is a basic amino acid (SEQ ID NO:11), CKAAK (SEQ ID NO:12), CKAAKN (SEQ ID NO:13) and KAAKN (SEQ ID NO:14). X$_1$ can be, for example, arginine, histidine and lysine.

In another embodiment, a peptide of the invention, as well as a peptide contained in a conjugate of the invention, contains at least 4 contiguous amino acids of the amino acid CKGAKAR (SEQ ID NO:19), or a conservative variant of peptidomimetic thereof. The peptide also can contain at least 5 contiguous amino acids of the amino acid sequence CKGAKAR (SEQ ID NO:19), at least 6 contiguous amino acids of the amino acid sequence CKGAKAR (SEQ ID NO:19), at least 7 contiguous amino acids of the amino acid sequence CKGAKAR (SEQ ID NO:19) or a conservative variant of peptidomimetic thereof. Exemplary peptide sequences that contain at least 4 contiguous amino acids of the amino acid sequence CKGAKAR (SEQ ID NO:19) include, but are not limited to AKAR (SEQ ID NO:16), GAKAR (SEQ ID NO:17), KGAKAR (SEQ ID NO:18), and CKGAKA (SEQ ID NO:20).

In a further embodiment, a peptide of the invention, as well as a peptide contained in a conjugate of the invention, contains at least 4 contiguous amino acids of the amino acid sequence VGVGEWSV (SEQ ID NO:35), or a conservative variant of peptidomimetic thereof. The peptide also can contain at least 5 contiguous amino acids of the amino acid sequence VGVGEWSV (SEQ ID NO:35), at least 6 contiguous amino acids of the amino acid sequence VGVGEWSV (SEQ ID NO:35), at least 7 contiguous amino acids of the amino acid sequence VGVGEWSV (SEQ ID NO:35), or at least 8 contiguous amino acids of the amino acid sequence VGVGEWSV (SEQ ID NO:35), or a conservative variant of peptidomimetic thereof. Exemplary peptide sequences that contain at least 4 contiguous amino acids of the amino acid sequence VGVGEWSV (SEQ ID NO:35) include, but are not limited to VGVG (SEQ ID NO:36), VGVGE (SEQ ID NO:37).

The invention also provides an isolated peptide or peptidomimetic that selectively homes to premalignant and malignant pancreatic vasculature. The peptide contains at least 4 contiguous amino acids of the amino acid sequence CRGRRST (SEQ ID NO:5) or FRVGVADV (SEQ ID NO:27), or a conservative variant or peptidomimetic thereof and has a length of less than 50 residues, such as less than 40 residues, less than 30 residues, less than 20 residues, less than 10 residues, and less than 8 residues.

In one embodiment, a peptide of the invention, as well as a peptide contained in a conjugate of the invention, contains at least 4 contiguous amino acids of the amino acid sequence CRGRRST (SEQ ID NO:5), or a conservative variant of peptidomimetic thereof. The peptide also can contain at least 5 contiguous amino acids of the amino acid sequence CRGRRST (SEQ ID NO:5), at least 6 contiguous amino acids of the amino acid sequence CRGRRST (SEQ ID NO:5), or at least 7 contiguous amino acids of the amino acid sequence CRGRRST (SEQ ID NO:5), or a conservative variant of peptidomimetic thereof. Exemplary peptide sequences that contain at least 4 contiguous amino acids of the amino acid sequence CRGRRST (SEQ ID NO:5) include, but are not limited to, RGRR (SEQ ID NO:1); RGRRS (SEQ ID NO:2); RGRRST (SEQ ID NO:3); and CRGRRS (SEQ ID NO:4).

In another embodiment, a peptide of the invention, as well as a peptide contained in a conjugate of the invention, contains at least 4 contiguous amino acids of the amino acid sequence FRVGVADV (SEQ ID NO:27), or a conservative variant of peptidomimetic thereof. The peptide also can contain at least 5 contiguous amino acids of the amino acid sequence FRVGVADV (SEQ ID NO:27), at least 6 contiguous amino acids of the amino acid sequence FRVGVADV (SEQ ID NO:27), at least 7 contiguous amino acids of the amino acid sequence FRVGVADV (SEQ ID NO:27), or at least 8 contiguous amino acids of the amino acid sequence FRVGVADV (SEQ ID NO:27). Exemplary peptide sequences that contain at least 4 contiguous amino acids of the amino acid sequence FRVGVADV (SEQ ID NO:27) include, but are not limited to, RVGV (SEQ ID NO:21), RVGVA (SEQ ID NO:22), RVGVAD (SEQ BD NO:23), VGVAD (SEQ ID NO:24), VGVADV (SEQ ID NO:25), and RVGVADV (SEQ ID NO:26).

As disclosed herein in Example V, a receptor for peptide sequence CRGRRST (SEQ ID NO:5) was identified as PDG-FRβ. Therefore, the invention provides an isolated peptide or peptidomimetic that selectively homes to premalignant and malignant pancreatic vasculature, wherein the peptide or peptidomimetic has an ability to bind to a PDGFRβ, and has a length of less than 50 residues. The isolated peptide or peptidomimetic can have, for example, a length of less than 40 residues, less than 30 residues, less than 20 residues, less than 10 residues, and less than 8 residues.

It is understood that a homing molecule useful in the invention can be, without limitation, a peptide or peptidomimetic. As used herein, the term "peptide" is used broadly to mean peptides, proteins, fragments of proteins and the like. The term "peptidomimetic," as used herein, means a peptide-like molecule that has the activity of the peptide upon which it is structurally based. Such peptidomimetics include chemically modified peptides, peptide-like molecules containing non-naturally occurring amino acids, and peptoids, and have an activity such as the selective homing activity of the peptide upon which the peptidomimetic is derived (see, for example, Goodman and Ro, *Peptidomimetics for Drug Design*, in "Burger's Medicinal Chemistry and Drug Discovery" Vol. 1 (ed. M. E. Wolff; John Wiley & Sons (1995), pages 803-861).

A variety of peptidomimetics are known in the art including, but not limited to, peptide-like molecules that contain a constrained amino acid, a non-peptide component that mimics peptide secondary structure, or an amide bond isostere. A peptidomimetic that contains a constrained, non-naturally occurring amino acid can include, without limitation, an α-methylated amino acid; α,α-dialkylglycine or α-aminocycloalkane carboxylic acid; an $N^\alpha$-$C^\alpha$ cyclized amino acid; an $N^\alpha$-methylated amino acid; a β- or γ-amino cycloalkane carboxylic acid; an α,β-unsaturated amino acid; a β,β-dimethyl or β-methyl amino acid; a β-substituted-2,3-methano amino acid; an N—$C^\delta$ or $C^\alpha$-$C^\delta$ cyclized amino acid; a substituted proline or another amino acid mimetic. A peptidomimetic that mimics peptide secondary structure can contain, without limitation, a nonpeptidic β-turn mimic; γ-turn mimic; mimic of β-sheet structure; or mimic of helical structure, each of which is well known in the art. As non-limiting examples, a peptidomimetic also can be a peptide-like molecule that contains an amide bond isostere such as a retro-inverso modification; reduced amide bond; methylenethioether or methylene-sulfoxide bond; methylene ether bond; ethylene bond; thioamide bond; trans-olefin or fluoroolefin bond; 1,5-disubstituted tetrazole ring; ketomethylene or fluoroketomethylene bond or another amide isostere. One skilled in the art understands that these and other peptidomimetics are encompassed within the meaning of the term "peptidomimetic" as used herein.

Methods for identifying a peptidomimetic are well known in the art and include, for example, the screening of databases that contain libraries of potential peptidomimetics. For example, the Cambridge Structural Database contains a collection of greater than 300,000 compounds that have known crystal structures (Allen et al., *Acta Crystallogr*. Section B, 35:2331 (1979)). This structural depository is continually updated as new crystal structures are determined and can be screened for compounds having suitable shapes, for example, the same shape as a peptide of the invention, as well as potential geometrical and chemical complementarity to a target molecule. Where no crystal structure of a peptide of the invention is available, a structure can be generated using, for example, the program CONCORD (Rusinko et al., *J. Chem. Inf. Comput. Sci*. 29:251 (1989)). Another database, the Available Chemicals Directory (Molecular Design Limited, Informations Systems; San Leandro, Calif.), contains about 100,000 compounds that are commercially available and also can be searched to identify potential peptidomimetics of a peptide of the invention, for example, with activity in selectively homing to vasculature of premalignant pancreas or pancreatic tumor cells and pancreatic tumor vasculature.

The peptides and peptidomimetics of the invention, including the bifunctional and multivalent peptides and peptidomimetics described herein below, can have a variety of lengths. A peptide or peptidomimetic of the invention, or the peptide or peptidomimetic portion of a conjugate of the invention, can have, for example, a relatively short length of less than 6, less than 7, less than 8, less than 9, less than 10, less than 12, less than 15, less than 20, less than 25, less than 30, less than 35, less than 40, less than 45, less than 50, less than 60, less than 70 or less than 80 residues. A peptide or peptidomimetic of the invention, or conjugate containing the peptide or peptidomimetic, also can be useful in the context of a significantly longer sequence as described further below. As used herein, the term "residue" refers to an amino acid or analog thereof.

In various embodiments, the peptide or peptidomimetic portion of the conjugate has a defined length. The peptide or peptidomimetic, or the peptide or peptidomimetic portion of the conjugate, can have, for example, a length of at most 10, at most 20, most 10, at most 30, most 10, at most 40, most 10, at most 50, most 10, at most 100, most 10, at most 150, most 10, at most 200, most 10, at most 250, most 10, at most 300, most 10, at most 400, most 10, at most 500, most 10, at most 600, most 10, at most 700, most 10, at most 800, most 10, at most 900, most 10, at most 1000 or most 10, at most 2000 residues. The peptide or peptidomimetic, or the peptide or peptidomimetic portion of the conjugate, also can have, for example, a length of less than 60, less than 50, less than 40, less than 30, less than 25, less than 20, less than 15, or less than 10 residues. It is understood that the term "peptide or peptidomimetic portion of the conjugate" means the total number of residues in the peptide or peptidomimetic and any contiguous protein, peptide or peptidomimetic, such as a therapeutic protein or pro-apoptotic peptide.

Chimeric Proteins

As disclosed herein, a peptide or peptidomimetic of the invention can maintain homing activity in the context of a significantly longer sequence. As a non-limiting example, the peptides referenced as SEQ ID NOS:5, 9, 15, 19, 27, 34 and 35 demonstrated homing to respective targets when fused to a phage coat protein, confirming that a peptide of the invention can have selective homing activity when embedded in a larger protein sequence (see Example I). Thus, the invention provides a chimeric protein containing a peptide or peptidomimetic of the invention, fused to a heterologous protein. In one embodiment, the invention provides a chimeric protein containing a peptide or peptidomimetic that selectively homes to vasculature of premalignant pancreas and contains at least 5 contiguous amino acids of an amino acid sequence selected from SEQ ID NO:9 or SEQ ID NO:34, or a conservative variant or peptidomimetic of one or these sequences, fused to a heterologous protein.

In another embodiment, the invention provides a chimeric protein containing a peptide or peptidomimetic that selectively homes to pancreatic tumor cells and pancreatic tumor vasculature and contains at least 5 contiguous amino acids of an amino acid sequence selected from SEQ ID NO:15, SEQ ID NO:19, or SEQ ID NO:35, or a conservative variant or peptidomimetic of one or these sequences, fused to a heterologous protein.

In a further embodiment, the invention provides a chimeric protein containing a peptide or peptidomimetic that selectively homes to premalignant and malignant pancreatic vasculature and contains at least 5 contiguous amino acids of an amino acid sequence selected from SEQ ID NO:5 or SEQ ID NO:27, or a conservative variant or peptidomimetic of one or these sequences, fused to a heterologous protein.

A variety of heterologous proteins can be fused to one of these peptides or peptidomimetics. The term "heterologous," as used herein in reference to a protein fused to a peptide or peptidomimetic of the invention, means a protein derived from a source other than the gene encoding the fused peptide or upon which the fused homing peptidomimetic is derived. A heterologous protein can be, without limitation, a heterologous protein having a therapeutic activity, an antibody or an antigen-binding fragment. A chimeric protein of the invention can have a variety of lengths including, but not limited to, up to 100, up to 200, up to 300, up to 400, up to 500, up to 800, up to 1000 or up to 2000 residues or more.

Bifunctional Peptides

The invention also provides bifunctional peptides that contain a peptide that selectively homes to vasculature of premalignant pancreas fused to a second peptide having a separate function. Also provided by the invention are bifunctional peptides that contain a peptide that selectively homes pancreatic tumor cells and pancreatic tumor vasculature fused to a second peptide having a separate function. Further provided by the invention are bifunctional peptides that contain a peptide that selectively homes to premaligant or malignant pancreatic vasculature fused to a second peptide having a separate function. Such bifunctional peptides have at least two functions conferred by different portions of the peptide and can, for example, display anti-angiogenic activity or pro-apoptotic activity in addition to selective homing activity. As non-limiting examples, the invention provides bifunctional peptides such as CRSRKG-GG-$_D$(KLAKLAK)$_2$, CEYQLDVE-GG-$_D$(KLAKLAK)$_2$, CRGRRST-GG-$_D$(KLAKLAK)$_2$, CKAAKNK-GG-$_D$(KLAKLAK)$_2$, FRVG-VADV-GG-$_D$(KLAKLAK)$_2$, CSRPPRSEC-GG-$_D$(KLAK-LAK)$_2$, VGVGEWSV-GG-$_D$(KLAKLAK)$_2$ or CKGAKAR-GG-$_D$(KLAKLAK)$_2$. In such peptides, the CRSRKG (SEQ ID NO:9), CEYQLDVE (SEQ ID NO:34), CRGRRST (SEQ ID NO:5), CKAAKNK (SEQ ID NO:15), FRVGVADV (SEQ ID NO:27), VGVGEWSV (SEQ ID NO:35), or CKGAKAR (SEQ ID NO:19) portion exhibits selective homing activity, while the $_D$(KLAKLAK)$_2$ portion exhibits pro-apoptotic activity.

Homing Molecules that are Antibodies

The conjugates and methods of the invention can be practiced with a homing antibody or antigen-binding fragment thereof that selectively homes to vasculature of premalignant pancreas; that selectively homes to pancreatic tumor cells and pancreatic tumor vasculature or that selectively homes to premalignant and malignant pancreatic vasculature. As used herein, the term "antibody" is used in its broadest sense to include polyclonal and monoclonal antibodies, as well as polypeptide fragments of antibodies that retain binding activity for the respective cognate receptor of at least about $1 \times 10^5$ M$^{-1}$. One skilled in the art understands that antibody fragments including, without limitation, Fab, F(ab')$_2$ and Fv fragments, can retain binding activity for a cognate receptor and, thus, are included within the definition of antibody. In addition, the term "antibody," as used herein, encompasses non-naturally occurring antibodies and fragments usually containing, at a minimum, one V$_H$ and one V$_L$ domain, such as chimeric antibodies, humanized antibodies and single chain Fv fragments (scFv) that specifically or selectively bind the appropriate cognate receptor. Such non-naturally occurring antibodies can be constructed using solid phase peptide synthesis, produced recombinantly or obtained by screening phage-displayed or other combinatorial libraries such as those consisting of variable heavy and light chains as described in Borrebaeck (Ed.), *Antibody Engineering* (Second edition) New York: Oxford University Press (1995)) using, for example, an assay described herein below.

Homing molecules that are antibodies also can be prepared using a cognate receptor fusion protein or a synthetic peptide encoding a portion of a cognate receptor. One skilled in the art understands that purified human or other cognate receptors, which can be produced recombinantly, including peptide portions of a cognate receptor such as synthetic peptide fragments can be used as immunogens. It is understood that fragments of the cognate receptor for an amino acid sequence selected from SEQ ID NOS:5, 9, 15, 19, 27, 34 or 35 useful as immunogens include fragments of the cognate receptor that serve to produce anti-cognate receptor antibodies that are readily internalized into cells expressing cell-surface cognate receptor for an amino acid sequence selected from SEQ ID NOS:5, 9, 15, 19, 27, 34 or 35. One skilled in the art further understands that non-immunogenic fragments or synthetic peptides of a cognate receptor for an amino acid sequence selected from SEQ ID NOS:5, 9, 15, 19, 27, 34 or 35 can be made immunogenic by coupling the hapten to a carrier molecule such as bovine serum albumin (BSA) or keyhole limpet hemocyanin (KLH). In addition, various other carrier molecules and methods for coupling a hapten to a carrier molecule are well known in the art as described, for example, by Harlow and Lane, *Antibodies: A Laboratory Manual* (Cold Spring Harbor Laboratory Press, 1988)).

Conjugates

The invention provides a conjugate that includes a therapeutic moiety linked to a peptide or peptidomimetic that selectively homes to vasculature of premalignant pancreas. The peptide or peptidomimetic contains at least 5 contiguous amino acids of an amino acid sequence selected from CRSRKG (SEQ ID NO:9) and CEYQLDVE (SEQ ID NO:34), or a conservative variant or peptidomimetic thereof. In embodiments of the invention, the peptide or peptidomimetic has a length of less than 100 residues, less tan 50 residues and less than 25 residues. Also provided by the invention is a conjugate containing a therapeutic moiety linked to a peptide or peptidomimetic that selectively homes to vasculature of premalignant pancreas, in which the peptide or peptidomimetic binds specifically to a cognate receptor for SEQ ID NO:9 or SEQ ID NO:34.

The invention additionally provides a conjugate containing a therapeutic moiety linked to a peptide or peptidomimetic that selectively homes to pancreatic tumor cells and pancreatic tumor vasculature, the peptide or peptidomimetic comprising at least 5 contiguous amino acids of an amino acid sequence selected from CKAAKNK (SEQ ID NO:15), CKGAKAR (SEQ ID NO:19), and VGVGEWSV (SEQ ID NO:35), or a conservative variant or peptidomimetic thereof. In embodiments of the invention, the peptide or peptidomimetic has a length of less than 100 residues, less than 50 residues and less than 25 residues. Also provided by the invention is a conjugate that contains therapeutic moiety linked to a peptide or peptidomimetic that selectively homes to pancreatic tumor cells and pancreatic tumor vasculature, wherein the peptide or peptidomimetic binds specifically to a cognate receptor for SEQ ID NO:15, SEQ ID NO:19 or SEQ ID NO:35.

The invention provides a conjugate that contains a therapeutic moiety linked to a peptide or peptidomimetic that selectively homes to premalignant and malignant pancreatic vasculature, the peptide or peptidomimetic containing at least 5 contiguous amino acids of an amino acid sequence selected from CRGRRST (SEQ ID NO:5) and FRVGVADV (SEQ ID NO:27), or a conservative variant or peptidomimetic thereof. In embodiments of the invention, the peptide or peptidomimetic has a length of less than 100 residues, less than 50 residues and less than 25 residues. Also provided by the invention is a conjugate that contains a therapeutic moiety linked to a peptide or peptidomimetic that selectively homes to pancreatic tumor cells and pancreatic tumor vasculature, wherein the peptide or peptidomimetic binds specifically to a cognate receptor for SEQ ID NO:5 or SEQ ID NO:27.

The conjugates and methods of the invention disclosed herein involve homing molecules. As used herein, the term "molecule" is used broadly to mean a polymeric or non-polymeric organic chemical such as a small molecule drug; a nucleic acid molecule such as an RNA, a cDNA or other DNA, or an oligonucleotide; a peptide or peptidomimetic; or a protein such as an antibody or a growth factor receptor or a fragment thereof such as an Fv, Fd, or Fab fragment of an antibody containing the antigen-binding domain.

The phrase "homing molecule that selectively homes to vasculature of premaligant pancreas," as used herein, means any molecule that preferentially localizes in vivo to vasculature of premalignant pancreas as compared to vasculature of malignant pancreas and vasculature of normal pancreas. Similarly, the phrase "peptide or peptidomimetic that selectively homes to vasculature of premalignant pancreas" means a peptide or peptidomimetic that preferentially localizes in vivo to vasculature of premalignant pancreas as compared to vasculature of malignant pancreas and vasculature of normal pancreas. As disclosed herein, such a homing molecule can be a peptide or peptidomimetic. It is understood that a peptide or peptidomimetic that selectively homes to vasculature of premalignant pancreas can home to the supporting vasculature of a variety of premalignant lesions in addition to premalignant pancreas, or can exhibit preferential homing to vasculature of premalignant lesions in a subset of tissue types including premalignant pancreas, or can exhibit significant homing exclusively to vasculature of premalignant pancreas.

Selective homing of a peptide or peptidomimetic that selectively homes to vasculature of premalignant pancreas generally is characterized by at least a two-fold greater localization within vasculature of premalignant pancreas as compared to vasculature of malignant pancreas and normal pancreatic vasculature. Such a peptide or peptidomimetic can be characterized, for example, by 5-fold, 10-fold, 20-fold or more greater localization within vasculature of premalignant pancreas as compared to vasculature of malignant pancreas and normal pancreatic vasculature. As discussed above, it is understood that a peptide or peptidomimetic that selectively homes to vasculature of premalignant pancreas can home, in part, to vasculature of one or more other premalignant tissues.

As used herein, the term "premalignant" means a precancerous state of a tissue having a an abnormality in which cancer is more likely to occur than in a normal tissue of the same type. Such an abnormality can be characterized based on histological abnormalities of cytology and/or architecture or biochemical differences between the precancerous versus normal states of the tissue. Particular differences depend on the particular type of tissue undergoing a premalignant process and are described in the art, for example, as metaplasia, dysplasia, hyperplasia, carcinoma in situ, angiogenic and the like, depending on the degree of structural and/or functional change compared to normal.

The phrase "homing molecule that selectively homes to pancreatic tumor cells and pancreatic tumor vasculature," as used herein, means any molecule that preferentially localizes in vivo to pancreatic tumor cells and pancreatic tumor vasculature as compared to premalignant pancreatic tumor cells and vasculature, and normal pancreatic tumor cells and vasculature. Similarly, the phrase "peptide or peptidomimetic that selectively homes to pancreatic tumor cells and pancreatic tumor vasculature" means a peptide or peptidomimetic that preferentially localizes in vivo to pancreatic tumor cells and pancreatic tumor vasculature as compared to premalignant pancreatic cells and vasculature, and normal pancreatic cells and vasculature. It is understood that a peptide or peptidomimetic that selectively homes to pancreatic tumor cells and pancreatic tumor vasculature can home to the supporting vasculature of a variety of malignant lesions in addition to pancreatic tumor cells and vasculature, or can exhibit preferential homing to vasculature of premalignant lesions in a subset of tissue types including premalignant pancreas, or can exhibit significant homing exclusively to pancreatic tumor cells and pancreatic tumor vasculature.

Selective homing of a peptide or peptidomimetic that selectively homes to pancreatic tumor cells and pancreatic tumor vasculature generally is characterized by at least a two-fold greater localization within pancreatic tumor cells and pancreatic tumor vasculature as compared to pancreatic premalignant cells and premalignant pancreatic vasculature and normal pancreatic cells and vasculature. Such a peptide or peptidomimetic can be characterized, for example, by 5-fold, 10-fold, 20-fold or more greater localization within pancreatic tumor cells and pancreatic tumor vasculature as compared to premalignant cells and premalignant pancreatic vasculature and normal pancreatic cells and vasculature. As discussed above, it is understood that a peptide or peptidomimetic that selectively homes to pancreatic tumor cells and pancreatic tumor vasculature can additionally localize to tumor cells and vasculature of one or more other malignant tissues in addition to selectively homing to pancreatic tumor cells and pancreatic tumor vasculature.

A peptide or peptidomimetic of the invention can be characterized by having the ability to preferentially localize to both premalignant and malignant pancreatic vasculature. Such a peptide or peptidomimetic can have greater selectivity for premalignant vasculature, greater selectivity for malignant vasculature, or can have similar selectivities for both premalignant and malignant vasculature. The phrase "homing molecule that selectively homes to premalignant and malignant pancreatic vasculature," as used herein, means any molecule that preferentially localizes in vivo to premalignant and malignant pancreatic vasculature as compared to normal pancreatic vasculature. Similarly, the phrase "peptide or peptidomimetic that selectively homes to premalignant and malignant pancreatic vasculature" means a peptide or peptidomimetic that preferentially localizes in vivo to premalignant and malignant pancreatic vasculature as compared to normal pancreatic vasculature. It is understood that a peptide or peptidomimetic that selectively homes to premalignant and malignant pancreatic vasculature can home to the supporting vasculature of a variety of premalignant and malignant lesions in addition to premalignant and malignant pancreatic vasculature, or can exhibit preferential homing to vasculature of premalignant and malignant lesions in a subset of tissue types including premalignant and malignant pancreas, or can exhibit significant homing exclusively to premalignant and malignant pancreatic vasculature. It is also understood that a peptide or peptidomimetic that selectively homes to premalignant and malignant pancreatic vasculature can home to tumor cells, such as pancreatic tumor cells, for example, via compromised, damaged or otherwise leaky malignant pancreatic vasculature.

Selective homing of a peptide or peptidomimetic that selectively homes to premalignant and malignant pancreatic vasculature generally is characterized by at least a two-fold greater localization within premalignant or malignant pancreatic vasculature as compared to vasculature of normal pancreas. Such a peptide or peptidomimetic can be characterized, for example, by 5-fold, 10-fold, 20-fold or more greater localization within premalignant and malignant pancreatic vasculature as compared to vasculature of normal pancreas. As discussed above, it is understood that a peptide or peptidomimetic that selectively homes to premalignant and malignant pancreatic vasculature can additionally localize to premalignant and malignant vasculature of one or more other tissues in addition to selectively homing to premalignant and malignant pancreatic vasculature. In addition, a peptide or peptidomimetic that selectively homes to vasculature of premalignant pancreas that also selectively homes, to a lesser extent, to pancreatic tumor cells and pancreatic tumor vasculature can be characterized as a peptide or peptidomimetic that selectively homes to premalignant and malignant pancreatic vasculature. Similarly, a peptide or peptidomimetic that selectively homes to pancreatic tumor cells and pancreatic tumor vasculature that also selectively homes, to a lesser extent, to premalignant pancreas can be characterized as a peptide or peptidomimetic that selectively homes to premalignant and malignant pancreatic vasculature.

Conservative Variants

The present invention also provides a peptide or peptidomimetic or conjugate containing a peptide or peptidomimetic that includes an amino acid sequence that is a conservative variant, for example, of at least five contiguous amino acids of an amino acid sequence selected from CRGRRST (SEQ ID NO:5), CRSRKG (SEQ ID NO:9); CKAAKNK (SEQ ID NO:15), CKGAKAR (SEQ ID NO:19), FRVGVADV (SEQ ID NO:27), CEYQLDVE (SEQ ID NO:34), and VGVGEWSV (SEQ ID NO:35). As used herein, a "conservative variant" is an amino acid sequence in which a first amino acid is replaced by a second amino acid or amino acid analog having at least one similar biochemical property, which can be, for example, similar size, charge, hydrophobicity or hydrogen-bonding capacity. For example, a first hydrophobic amino acid can be conservatively substituted with a second (non-identical) hydrophobic amino acid such as alanine, valine, leucine, or isoleucine, or an analog thereof. Similarly, a first basic amino acid can be conservatively substituted with a second basic amino acid such as arginine or lysine, or an analog thereof. In the same way, a first acidic amino acid can be conservatively substituted with a second acidic amino acid such as aspartic acid or glutamic acid, or an analog thereof, or an aromatic amino acid such as phenylalanine can be conservatively substituted with a second aromatic amino acid or amino acid analog, for example, tyrosine.

Multivalent Conjugates

The invention provides a multivalent conjugate, containing a therapeutic moiety linked to at least two peptides or peptidomimetics that selectively home to vasculature of premalignant pancreas, each of the peptides or peptidomimetics containing at least 5 contiguous amino acids of an amino acid sequence selected from CRSRKG (SEQ ID NO:9) and CEYQLDVE (SEQ ID NO:34).

The invention further provides a multivalent conjugate that contains a therapeutic moiety linked to at least two peptides or peptidomimetics that selectively home to pancreatic tumor cells and pancreatic tumor vasculature, each of the peptides or peptidomimetics containing at least 5 contiguous amino acids of an amino acid sequence selected from CKAAKNK (SEQ ID NO:15), CKGAKAR (SEQ ID NO:19), and VGVGEWSV (SEQ ID NO:35), or a conservative variant or peptidomimetic thereof.

The invention provides a multivalent conjugate that contains a therapeutic moiety linked to at least two peptides or peptidomimetics that selectively home to premalignant and malignant vasculature, each of the peptides or peptidomimetics containing at least 5 contiguous amino acids of an amino acid sequence selected from CRGRRST (SEQ ID NO:5) and FRVGVADV (SEQ ID NO:27), or a conservative variant or peptidomimetic thereof.

A multivalent conjugate of the invention containing multiple peptide or peptidomimetics can include, for example, two or more, three or more, five or more, ten or more, twenty or more, thirty or more, forty or more, fifty or more, 100 or more, 200 or more, 300 or more, 400 or more, 500 or more or 1000 or more peptides or peptidomimetics. In one embodiment, the peptides or peptidomimetics have an identical amino acid sequence. In another embodiment, the multivalent conjugate includes peptides or peptidomimetics having non-identical amino acid sequences.

A multivalent conjugate of the invention can be linked to a variety of moieties. Moieties useful in a multivalent conjugate of the invention include, without limitation, phage, retroviruses, adenoviruses, adeno-associated viruses and other viruses, cells, liposomes, polymeric matrices, non-polymeric matrices or particles such as gold particles, microdevices and nanodevices, and nano-scale semiconductor materials.

Liposomes consisting, without limitation, of phospholipids or other lipids, are nontoxic, physiologically acceptable and metabolizable carriers that are readily made to be incorporated into a conjugate of the invention (Gregoriadis, *Liposome Technology*, Vol. 1 (CRC Press, Boca Raton, Fla. (1984)). It is understood that the liposome or other polymeric matrix additionally can include one or more other components if desired, such as, without limitation, one or any combination of therapeutic agents, anti-angiogenic agents or cytotoxic agents.

As disclosed herein, peptides CEYQLDVE (SEQ ID NO:34) and CRSRKG (SEQ ID NO:9) recognize a target "receptor" that is expressed in vasculature of premalignant pancreas but is essentially absent or inaccessible for binding via the circulation in vasculature of malignant pancreas or normal pancreas. Also as disclosed herein, peptides CKAAKNK (SEQ ID NO:15); CKGAKAR (SEQ ID NO:19); and VGVG (SEQ ID NO:36) recognize a target "receptor" that is expressed in pancreatic tumor cells and pancreatic tumor vasculature but is essentially absent or inaccessible for binding via the circulation in the vasculature or premalignant pancreas or normal pancreas. Further, as disclosed herein, peptides CRGRRST (SEQ ID NO:5) or FRVGVADV (SEQ ID NO:27) recognize a target "receptor" that is expressed in premalignant and malignant pancreatic vasculature but is essentially absent or inaccessible for binding via the circulation in the vasculature of normal pancreas. The cell surface and cell-type selective expression of the target receptor form the basis for the selective homing activity of the specific peptides described above and related peptides, peptidomimetics and other molecules.

Based on these discoveries, it is clear that molecules structurally unrelated to SEQ ID NOS: 9 or 34 but that bind the same cognate receptors also have the same characteristic of selectively homing to vasculature of premalignant pancreas and other premalignant tissues. Such molecules can be identified by the ability to specifically bind to, or to compete with SEQ ID NO:9 or 34 for specific binding to cells expressing their respective cognate receptors. It is also clear that molecules structurally unrelated to SEQ ID NOS:15 and 19 but that bind the same cognate receptors also have the same characteristic of selectively homing to pancreatic tumor cells and pancreatic tumor vasculature and cells and vasculature of other malignant tissues. Such molecules can be identified by the ability to specifically bind to, or to compete with SEQ ID NOS:15 or 19 for specific binding to cells expressing their respective cognate receptors. Further, it is clear that molecules structurally unrelated to SEQ ID NOS:5, 27 or 35 but that bind the same cognate receptors also have the same characteristic of selectively homing to premalignant and malignant pancreatic vasculature and premalignant and malignant vasculature of other tissues. Such molecules can be identified by the ability to specifically bind to, or to compete with SEQ ID NOS:5, 27 or 35 for specific binding to cells expressing their respective cognate receptors. Selective homing to vasculature of premalignant pancreas; pancreatic tumor cells and pancreatic tumor vasculature; or premalignant and malignant pancreatic vasculature, readily can be confirmed using in vivo panning as disclosed herein in Example I (see, also, U.S. Pat. No. 5,622,699).

A homing molecule of the invention, such as a peptide or peptidomimetic, specifically binds the indicated cognate receptor. As used herein, the term "specifically binds" or "specifically binding" means binding that is measurably different from a non-specific interaction. Specific binding can be measured, for example, by determining binding of a molecule compared to binding of a control molecule, which generally is a molecule of similar structure that does not have binding activity. In this case, specific binding is indicated if the molecule has measurably higher affinity for cells expressing the cognate receptor, for example, than for cells that do not express the cognate receptor. Specificity of binding can be determined, for example, by competitive inhibition of the binding of a known binding molecule such SEQ ID NO:9 or 34 to identify molecules that selectively home to vasculature of premalignant pancreas; by competitive inhibition of the binding of a known binding molecule such as SEQ ID NO:15, 19 or 35 to identify molecules that selectively home to pancreatic tumor cells and pancreatic tumor vasculature; or by competitive inhibition of the binding of a known binding molecule such as SEQ ID NO:5 or 27 to identify molecules that selectively home to premalignant and malignant pancreatic vasculature.

The term "binds specifically," as used herein, includes both low and high affinity specific binding. Specific binding can be exhibited, for example, by a low affinity homing molecule having a Kd of at least about $10^{-4}$ M. For example, if the cognate receptor has more than one binding site, a homing molecule having low affinity can be useful for targeting, for example, vasculature of premalignant pancreas; pancreatic tumor cells and pancreatic tumor vasculature; or premaligant and malignant pancreatic vasculature. Specipfic binding also can be exhibited by a high affinity homing molecule, for example, a homing molecule having a Kd of at least about $10^{-5}$ M. Such a molecule can have, for example, a Kd of at least about $10^{-6}$ M, at least about $10^{-7}$ M, at least about $10^{-8}$ M, at least about $10^{-9}$ M, at least about $10^{-10}$ M, or can have a Kd of at least about $10^{-11}$ M or $10^{-12}$ M or greater. Both low and high affinity homing molecules are useful and are encompassed by the invention. Low affinity homing molecules are useful in targeting, for example, multivalent conjugates such as viruses and other particles. High affinity homing molecules are useful in targeting, for example, multivalent and univalent conjugates.

Thus, the invention further provides a conjugate that contains a therapeutic moiety linked to a peptide or peptidomimetic that selectively homes to vasculature of premalignant pancreas and that specifically binds a cognate receptor for SEQ ID NO:9 or 34. Also provided is a conjugate that contains a therapeutic moiety linked to a peptide or peptidomimetic that selectively homes to pancreatic tumor cells and pancreatic tumor vasculature and which specifically binds a cognate receptor for an amino acid sequence selected from SEQ ID NO:15, 19 or 35. Further provided is a conjugate that contains a therapeutic moiety linked to a peptide or peptidomimetic that selectively homes to premalignant and malignant pancreatic vasculature and that specifically binds a cognate receptor for SEQ ID NO:5 or 27. As is shown herein in Example V, the PDGFRβ is a cognate receptor for SEQ ID NO:5. Thus, in one embodiment, the conjugate contains a peptide or peptidomimetic that specifically binds PDGFRβ.

In one embodiment, any of such conjugates can contain a peptide or peptidomimetic that is not an antibody or antigen-binding fragment thereof. In another embodiment, the peptide or peptidomimetic portion of the conjugate can have a length of at most 200 residues, or a length of at most 50 residues.

The invention provides method of directing a moiety to a pancreatic premalignant lesion in an individual. The method involves administering to the individual a conjugate containing a moiety linked to (a) a peptide or peptidomimetic that selectively homes to vasculature of premalignant pancreas, the peptide or peptidomimetic containing at least 5 contiguous amino acids of an amino acid sequence selected from CRSRKG (SEQ ID NO:9) and CEYQLDVE (SEQ ID NO:34), or a conservative variant or peptidomimetic thereof, or (b) a peptide or peptidomimetic that selectively homes to premalignant and malignant pancreatic vasculature, the peptide or peptidomimetic containing at least 5 contiguous amino acids of an amino acid sequence selected from CRGRRST (SEQ ID NO:5) and FRVGVADV (SEQ ID NO:27), or a conservative variant or peptidomimetic thereof, thereby directing the moiety to the vasculature of the pancreatic premalignant lesion. In one embodiment, the moiety is a therapeutic moiety, such as an angiogenic inhibitor. In another embodiment, the moiety is a diagnostic moiety. Exemplary moieties useful in this method are described herein below.

The invention also provides a method of directing a moiety to pancreatic tumor cells and pancreatic tumor vasculature in an individual. The method involves administering to the individual a conjugate containing a moiety linked to: (a) a peptide or peptidomimetic that selectively homes to pancreatic tumor cells and pancreatic tumor vasculature, the peptide or peptidomimetic containing at least 5 contiguous amino acids of an amino acid sequence selected from CKAAKNK (SEQ ID NO:15), CKGAKAR (SEQ ID NO:19), FRVGVADV (SEQ ID NO:27)and VGVGEWSV (SEQ ID NO:35), or a conservative variant or peptidomimetic thereof, or (b) a peptide or peptidomimetic that selectively homes to premalignant and malignant pancreatic vasculature, the peptide or peptidomimetic containing at least 5 contiguous amino acids of an amino acid sequence selected from CRGRRST (SEQ ID NO:5) and FRVGVADV (SEQ ID NO:27), or a conservative variant or peptidomimetic thereof, thereby directing the moiety to pancreatic tumor cells and pancreatic tumor vasculature.

Imaging

Selective delivery of diagnostic agents to vasculature that supports tumors provides a tool for diagnosis of early or late stage cancers, such pancreatic cancer. The pancreas is an organ of the digestive system that contains exocrine and endocrine components. The exocrine component is a compound gland with branched ducts and serous secretory units. The endocrine component synthesizes and secretes into the blood, hormones that regulate glucose, lipid and protein metabolism of the body. This component is dispersed within the exocrine component as distinct cell masses called islets of Langerhans. Islets of Langerhans are polygonal endocrine cells arranged in short, irregular cords that are profusely invested with a network of fenestrated capillaries. As is shown herein, a peptide or peptidomimetic of the invention can be used to distinguish between normal pancreatic vasculature and premalignant or malignant pancreatic vasculature. Therefore, when linked to a detectable moiety, a peptide or peptidomimetic of the invention can be used to visualize, or otherwise render detectable, early changes in pancreatic vascular associated with a precancerous state, as well as later changes in pancreatic vascular associated with a more advanced or malignant state.

The invention provides a method for imaging pancreatic premalignant lesions in an individual. The method involves: (a) administering to the individual a conjugate containing a detectable moiety linked to a peptide or peptidomimetic that selectively homes to vasculature of premalignant pancreas, the peptide or peptidomimetic containing at least 5 contiguous amino acids of an amino acid sequence selected from CRSRKG (SEQ ID NO:9) and CEYQLDVE (SEQ ID NO:34), or a conservative variant or peptidomimetic thereof, and (b) detecting the conjugate, thereby imaging pancreatic premalignant lesions.

The invention also provides a method of imaging pancreatic tumors and pancreatic tumor vasculature in an individual. The method involves (a) administering to the individual a conjugate containing a detectable moiety linked to a peptide or peptidomimetic that selectively homes to pancreatic tumor cells and pancreatic tumor vasculature, the peptide or peptidomimetic containing at least 5 contiguous amino acids of an amino acid sequence selected from CKAAKNK (SEQ ID NO:15) and CKGAKAR (SEQ ID NO:19), or a conservative variant or peptidomimetic thereof, and (b) detecting the conjugate, thereby imaging the pancreatic tumors and pancreatic tumor vasculature.

As used herein, the term "detectable moiety" means any molecule that can be administered in vivo and subsequently detected. Exemplary detectable moieties useful in the conjugates and methods of the invention include, without limitation, radiolabels and fluorescent molecules. Exemplary radionuclides include indium-111, technetium-99, carbon-11, and carbon-13. Fluorescent molecules include, without limitation, fluorescein, allophycocyanin, phycoerythrin, rhodamine, and Texas red.

The methods of the invention for imaging the vasculature of a premalignant tissue such as premalignant pancreas, or for imaging of tumor cells and tumor vasculature, such as pancreatic tumor cells and pancreatic rumor vasculature can be useful for early detection of premalignant lesions or malignancies including but not limited to, pancreatic premalignant lesions and tumors. Following administration of a conjugate of the invention containing a detectable moiety, the vasculature of premalignant tissue or tumor tissue is visualized. If the image is positive for the presence of such vasculature, further evaluation can be performed for the size of the tumor, if any, and the quantity of vascular infiltration. These results provide valuable information to the clinician with regard to the stage of development of the cancer and the presence or probability of metastasis. It is understood that the methods of the invention are application to a variety of types of premalignant lesions and cancers of organs including, yet not limited to, cancers of digestive tract, such as head and neck cancers, esophageal cancer, stomach cancer, pancreatic cancer, liver cancer, colon and rectal cancer, anal cancer; cancers of genital and urinary systems, such as kidney cancer, bladder cancer, testicular cancer, prostate cancer; cancers of the nervous system, such as brain cancer; bone cancer; nasopharyngeal cancer; retroperitoneal sarcomas; soft tissue cancers; thyroid cancer; breast cancer; ovarian cancer; gynecological cancers; choriocarcinoma and other types of cancers.

In a method of the invention for imaging vasculature of a premalignant tissue, the conjugate administered contains a detectable moiety that allows detection or visualization of the vasculature of the premalignant tissue such as a pancreatic premalignant lesion. In a method of the invention for imaging calls and vasculature of a malignant tissue, the conjugate administered contains a detectable moiety that allows detection or visualization of pancreatic tumors and pancreatic tumor vasculature. For such in vivo diagnostic imaging, a peptide or peptidomimetic is linked to a detectable moiety that, upon administration to the subject, is detectable external to the subject. Such a detectable moiety can be, for example, a gamma ray emitting radionuclide such as indium-113, indium-115 or technetium-99; following administration to a subject, the conjugate can be visualized using a solid scintillation detector.

A detectable moiety useful in the invention can be, for example, a paramagnetic ion such as a magnesium, manganese, iron oxide, dysprosium or gadolinium ion. Exemplary iron oxides include dextran-coated superparamagnetic iron oxide, carboxydextran-coated superparamagnetic iron oxide, ultrasmall superparamagnetic iron oxide, monocrystalline iron oxide nanocompound and ferromagnetic iron lignosulfonate. Exemplary gadolinium-based paramagnetic moieties include Gd-DTPA, dextran-Gd-DTPA, Gd-DTPA-24-cascade-polymer, Gd-DTPA-polylysine, Gd-melanin polymer and 6-dendrimer-Gd-DTPA. When linked to a peptide or peptidomimetic of the invention, such a paramagnetic ion can be used for enhanced magnetic resonance imaging (MRI). A paramagnetic ion can be linked directly to a peptide or peptidomimetic or linked indirectly, for example, by being contained in a liposome that is linked to the peptide or peptidomimetic.

A detectable moiety also can be an agent that facilitates detection of premalignant and malignant tissue in vitro. For example, a conjugate can contain a peptide or peptidomimetic of the invention linked to an enzyme, which produces a visible signal when an appropriate substrate is present. A detectable moiety useful in such a conjugate can be, for example, alkaline phosphatase or luciferase or the like, and can be detected by immunohistochemistry using routine techniques.

Therapy

The invention provides a method of treating a pancreatic premalignant lesion in an individual. The method involves administering to the individual a conjugate containing a therapeutic moiety linked to: (a) a peptide or peptidomimetic that selectively homes to premalignant and malignant pancreatic vasculature, the peptide or peptidomimetic containing at least 5 contiguous amino acids of an amino acid sequence selected from CRGRRST (SEQ ID NO:5), and FRVGVADV (SEQ ID NO:27), or a conservative variant or peptidomimetic thereof, or (b) a peptide or peptidomimetic that selectively homes to vasculature of premalignant pancreas containing at least 5 contiguous amino acids of an amino acid sequence selected from CRSRKG (SEQ ID NO:9) and CEYQLDVE (SEQ ID NO:34), thereby directing the therapeutic moiety to the pancreatic premalignant lesion in the individual to treat the pancreatic premalignant lesion. In one embodiment, the moiety is a therapeutic moiety, such as an angiogenic inhibitor. In one embodiment, the peptide or peptidomimetic selectively homes to vasculature of premalignant pancreas.

The invention also provides a method of reducing the severity of pancreatic cancer in an individual. The method involves administering to the individual a conjugate containing a therapeutic moiety linked to: (a) a peptide or peptidomimetic that selectively homes to pancreatic tumor cells and pancreatic tumor vasculature, the peptide or peptidomimetic containing at least 5 contiguous amino acids of an amino acid sequence selected from CKAAKNK (SEQ ID NO:15), CKGAKAR (SEQ ID NO:19), FRVGVADV and VGVGEWSV (SEQ ID NO:35), or a conservative variant or peptidomimetic thereof, or (b) a peptide or peptidomimetic that selectively homes to premalignant and malignant pancreatic vasculature, the peptide or peptidomimetic containing at least 5 contiguous amino acids of an amino acid sequence selected from CRGRRST (SEQ ID NO:5) and FRVGVADV (SEQ ID NO:27), or a conservative variant or peptidomimetic thereof, thereby directing the therapeutic moiety to pancreatic tumor cells or pancreatic tumor vasculature in the individual to reduce the severity of the pancreatic cancer.

Therapeutic Moieties

A variety of therapeutic moieties are useful in the conjugates and methods of the invention, including, without limitation, anti-angiogenic agents and cytotoxic agents, such as those that target a DNA-associated process. As used herein, the term "therapeutic moiety" is used broadly to mean a physical, chemical, or biological material that can be linked to a homing molecule and that alters biological activity in a normal or pathologic tissue upon administration. A therapeutic moiety, therefore, is potentially useful for the treatment of disease conditions. A therapeutic moiety can be any natural or nonnatural material including a biological material, such as a cell or phage; an organic chemical, such as a small molecule; a radionuclide; a nucleic acid molecule or oligonucleotide; a polypeptide; or a peptide or peptidomimetic. Therapeutic moieties useful in the invention include, without limitation, anti-angiogenic agents; cancer chemotherapeutic agents; cytotoxic agents; pro-apoptotic agents. A therapeutic moiety useful in the invention can be expressed on, contained in, or linked to any of the following: phage or other virus, cell, liposome, polymeric or non-polymeric matrix, gold or other particle, or a microdevice, nanodevice, or nano-scale semiconductor material. These and other materials known in the art can be components of the conjugates of the invention.

A therapeutic moiety useful in a conjugate of the invention can be, for example, an anti-angiogenic agent. As used herein, the term "anti-angiogenic agent" means a molecule that reduces or inhibits angiogenesis. An anti-angiogenic agent useful in the conjugates and methods of the invention can be, for example, an inhibitor or neutralizing antibody that reduces the expression or signaling of an angiogenic factor such as vascular endothelial growth factor (VEGF), which is a major inducer of angiogenesis in normal and pathological conditions, and is essential in embryonic vasculogenesis. The biological effects of VEGF include stimulation of endothelial cell proliferation, survival, migration and tube formation, and regulation of vascular permeability. An anti-angiogenic agent also can inhibit another angiogenic factor such as a member of the fibroblast growth factor (FGF) family such as FGF-1 (acidic), FGF-2 (basic), FGF-4 or FGF-5 (Slavin et al., *Cell Biol. Int.* 19:431-444 (1995); Folkman and Shing, *J. Biol. Chem.* 267:10931-10934 (1992)) or angiopoietin-1, a factor that signals through the endothelial cell-specific Tie2 receptor tyrosine kinase (Davis et al., *Cell* 87:1161-1169 (1996); and Suri et al., *Cell* 87:1171-1180 (1996)), or the receptor of one of these angiogenic factors. It is understood that a variety of mechanisms can act to inhibit activity of an angiogenic factor including, without limitation, direct inhibition of receptor binding or of secretion of the angiogenic factor into the extracellular space, and inhibition of signaling, expression or function of the angiogenic factor.

A variety of anti-angiogenic agents useful in the invention are known in the art and can be prepared by routine methods. See, for example, Hagedorn and Bikfalvi, *Crit. Rev. Oncol. Hematol.* 34:89-110 (2000) and Kirsch et al., *J. Neurooncol.* 50:149-163 (2000). Anti-angiogenic agents include, without limitation, small molecules; proteins such as angiogenic factors and receptors, transcription factors, and antibodies and antigen-binding fragments thereof; peptides and peptidomimetics; and nucleic acid molecules including ribozymes, antisense oligonucleotides, and nucleic acid molecules encoding, for example, dominant negative angiogenic factors and receptors, transcription factors, and antibodies and antigen-binding fragments thereof. Exemplary anti-angiogenic agents useful in the conjugates and methods of the invention include, yet are not limited to, angiostatin, endostatin, metastatin and 2ME2 (EntreMed; Rockville, Md.); anti-VEGF antibodies such as Avastin (Genentech; South San Francisco, Calif.); VEGFR-2 inhibitors such as the small molecules SU5416 and SU6668, (SUGEN; South San Francisco, Calif.); heparin-binding fragments of fibronectin; modified forms of antithrombin; collagenase inhibitors; basement membrane turnover inhibitors; angiostatic steroids; platelet factor 4, and fragments and peptides thereof; thrombospondin, and fragments and peptides thereof; and doxorubicin (O'Reilly et al., *Cell* 79:315-328 (1994)); O'Reilly et al., *Cell* 88: 277-285 (1997); Homandberg et al., *Am. J. Path.* 120:327-332 (1985); *Biochim. Biophys. Acta* 874:61-71 (1986); and O'Reilly et al., *Science* 285:1926-1928 (1999)). It is understood that these as well as other anti-angiogenic agents known in the art or that can be prepared by routine methods are encompassed by the term "anti-angiogenic agent" and can be used in the various conjugates and methods of the invention.

It is understood by those skilled in the art that an anti-angiogenic agent can be particularly efficacious when targeted to a specific stage of tumor progression (see, for example, Bergers et al., *Science* 284:808-812 (1999); and Bergers et al., *J. Clin. Invest.* 111:1287-1295 (2003)). Thus, in one embodiment, an anti-angiogenic agent useful in the invention is "effective against premalignant vasculature." As used herein, the term "anti-angiogenic agent effective against premalignant vasculature" means an angiogenic agent that can significantly reduce the number of angiogenic lesions during the premalignant phase of carcinogenesis, before solid tumors have formed. Such an anti-angiogenic agent is an anti-angiogenic agent effective against premalignant vasculature whether or not the agent also significantly reduces tumor burden or extends life-span in animals with tumors, including animals with small solid tumors or animals having large tumors and end-stage disease. As non-limiting examples, an anti-angiogenic agent effective against pre-malignant vasculature can be BB-94 (batimastat), a broad-spectrum inhibitor of matrix metalloproteinases (Talbot and Brown, *Eur. J. Cancer* 32A: 2528 (1996)); SU5416 (SUGEN), a small molecule inhibitor of VEGFR-2; or endostatin, a carboxy-terminal fragment of collagen XVIII (O'Reilly et al., *Cell* 88: 277 (1997); and Boehm et al., *Nature* 390: 404 (1997)), alone or combined with angiostatin, an internal fragment of plasminogen (O'Reilly et al., *Cell* 79: 314 (1994); and O'Reilly et al., *Nature Med.* 2: 689 (1996)). See, also, Bergers et al., supra, 1999; Bergers et al., supra, 2003.

An anti-angiogenic agent useful in the invention also can be an anti-angiogenic agent effective against tumor vasculature. As used herein, the term "anti-angiogenic agent effective against tumor vasculature" means an angiogenic agent that can significantly reduce tumor burden or extend life-span of animals having solid, vascularized tumors. Such an anti-angiogenic agent is an anti-angiogenic agent effective against tumor vasculature if there is efficacy against one or more of the following: small solid tumors, tumors with well-defined margins, invasive tumors or end-stage cancer, whether or not the agent significantly reduces the number of angiogenic lesions during the pre-malignant phase of carcinogenesis. As non-limiting examples, an anti-angiogenic agent effective against tumor vasculature can be efficacious only against small vascularized tumors, or against large tumors as well as small vascularized tumors. An anti-angiogenic agent effective against tumor vasculature can be, without limitation, an anti-angiogenic agent such as BB-94 (batimastat), endostatin, or angiostatin, which is effective against small tumors without significant efficacy on the large tumors characteristic of end-stage cancer (Bergers et al., supra, 1999). An anti-angiogenic agent effective against tumor vasculature further can be an anti-angiogenic agent effective against small tumors as well as large tumors in animals with short life expectancy such as, without limitation, AGM-1470 (TNP470), a small molecule inhibitor of endothelial cell proliferation (Ingber et al., Nature 348:555 (1990); Griffith et al., Chem. Biol. 4:461 (1997); Sin et al., Proc. Natl. Acad. Sci. U.S.A. 94:6099 (1997); and Castronovo and Belotti, Eur. J. Cancer 32A:2520 (1996)).

A therapeutic moiety useful in a conjugate of the invention can be, for example, a cytotoxic agent. As used herein, the term "cytotoxic agent" means any molecule that results in cell death by any mechanism. Exemplary cytotoxic agents useful in a conjugate of the invention encompass, without limitation, taxanes such as docetaxel; anthracyclins such as doxorubicin; alkylating agents; vinca alkaloids; anti-metabolites; platinum agents such as cisplatin or carboplatin; steroids such as methotrexate; antibiotics such as adriamycin; antimicrobial peptides, described herein below; and other cancer chemotherapeutic agents, which are chemical agents that inhibit the proliferation, growth, life-span or metastatic activity of cancer cells.

Effective cytotoxic agents useful in the invention include those that target DNA, for example, alkylating agents, agents that intercalate into DNA, and agents that result in double-stranded DNA breaks. Exemplary DNA-targeted drugs include, without limitation, cyclophosphamide, melphalan, mitomycin C, bizelesin, cisplatin, doxorubicin, etoposide, mitoxantrone, SN-38, Et-743, actinomycin D, bleomycin, TLK286 and SGN-15 (Hurley, supra, 2002). It is understood that DNA-targeting cytotoxic agents can be particular useful when combined in conjugates with a homing molecule that localizes, at least in part, to the nuclei of cells. Thus, in one embodiment the invention provides a conjugate containing a therapeutic moiety linked to a peptide or peptidomimetic that selectively homes to vasculature of premalignant pancreas and contains at least 5 contiguous amino acids of an amino acid sequence selected from CRSRKG (SEQ ID NO:9) and CEYQLDVE (SEQ ID NO:34), or a conservative variant or peptidomimetic thereof, where the therapeutic moiety is a cytotoxic agent that targets a DNA-associated process. In a further embodiment, the invention provides a conjugate containing a therapeutic moiety linked to a peptide or peptidomimetic that selectively homes to pancreatic tumor cells and pancreatic tumor vasculature and contains at least 5 contiguous amino acids of an amino acid sequence selected from CKAAKNK (SEQ ID NO:15), CKGAKAR (SEQ ID NO:19), and VGVGEWSV (SEQ ID NO:35), or a conservative variant or peptidomimetic thereof. Useful cytotoxic agents that target a DNA-associated process include, without limitation, alkylating agents, anti-tumor antibiotics and sequence-selective agents and further encompass agents such as cyclophosphamide, melphalan, mitomycin C, bizelesin, cisplatin, doxorubicin, etoposide, mitoxantrone, SN-38, Et-743, actinomycin D, bleomycin and TLK286.

Taxanes are cytotoxic agents useful in a conjugate of the invention. Useful taxanes include, without limitation, docetaxel (Taxotere; Aventis Pharmaceuticals, Inc.; Parsippany, N.J.) and paclitaxel (Taxol; Bristol-Myers Squibb; Princeton, N.J.). See, for example, Chan et al., J. Clin. Oncol. 17:2341-2354 (1999), and Paridaens et al., J. Clin. Oncol. 18:724 (2000).

A cytotoxic agent useful in a conjugate of the invention also can be an anthracyclin such as doxorubicin, idarubicin or daunorubicin. Doxorubicin is a commonly used cancer chemotherapeutic agent (Stewart and Ratain, In: "Cancer: Principles and practice of oncology" 5th ed., chap. 19 (eds. DeVita, Jr., et al.; J. P. Lippincott 1997); Harris et al., In "Cancer: Principles and practice of oncology," supra, 1997). In addition, doxorubicin has anti-angiogenic activity that can contribute to its effectiveness in treating cancer (Folkman, supra, 1997; Steiner, In "Angiogenesis: Key principles-Science, technology and medicine," pp. 449-454 (eds. Steiner et al.; Birkhauser Verlag, 1992)).

An alkylating agent such as melphalan or chlorambucil also can be a cytotoxic agent useful in a conjugate of the invention. Similarly, a vinca alkaloid such as vindesine, vinblastine or vinorelbine; or an antimetabolite such as 5-fluorouracil, 5-fluorouridine or a derivative thereof can be a cytotoxic agent that can be linked to a homing molecule in a conjugate of the invention.

Cytotoxic agents useful in the conjugates of the invention also include, without limitation, platinum agents. Such a platinum agent can be, for example, cisplatin or carboplatin as described, for example, in Crown, Seminars in Oncol. 28:28-37 (2001). Other cytotoxic agents useful in a conjugate of the invention include, but are not limited to, methotrexate, mitomycin-C, adriamycin, ifosfamide and ansamycins.

A cytotoxic agent also can be, for example, an antimicrobial peptide. In one embodiment, the invention provides a conjugate in which a peptide or peptidomimetic that selectively homes to vasculature of premalignant pancreas that is linked to an antimicrobial peptide, where the conjugate is selectively internalized by vasculature of a As used herein, the term "antimicrobial peptide" means a naturally occurring or synthetic peptide having antimicrobial activity, which is the ability to kill or slow the growth of one or more microbes and that has low mammalian cell toxicity when not linked to a homing molecule. An antimicrobial peptide can kill or slow the growth of, for example, one or more strains of bacteria including a Gram-positive or Gram-negative bacteria, or a fungi or protozoa. Thus, an antimicrobial peptide can have, for example, bacteriostatic or bacteriocidal activity against, for example, one or more strains of Escherichia coli, Pseudomonas aeruginosa or Staphylococcus aureus. While not wishing to be bound by the following, an antimicrobial peptide can have biological activity due to the ability to form ion channels through membrane bilayers as a consequence of self-aggregation.

An antimicrobial peptide is typically highly basic and can have a linear or cyclic structure. As discussed further below, an antimicrobial peptide can have an amphipathic α-helical structure (see U.S. Pat. No. 5,789,542; Javadpour et al., J. Med. Chem. 39:3107-3113 (1996); and Blondelle and Houghten, Biochem. 31: 12688-12694 (1992). An antimicrobial peptide also can be, for example, a β-strand/sheet-forming peptide as described in Mancheno et al., J. Peptide Res. 51:142-148 (1998).

An antimicrobial peptide can be a naturally occurring or synthetic peptide. Naturally occurring antimicrobial peptides have been isolated from biological sources such as bacteria, insects, amphibians, and mammals and are thought to represent inducible defense proteins that can protect the host organism from bacterial infection. Naturally occurring antimicrobial peptides include the gramicidins, magainins, mellitins, defensins and cecropins (see, for example, Maloy and Kari, *Biopolymers* 37:105-122 (1995); Alvarez-Bravo et al., *Biochem. J.* 302:535-538 (1994); Bessalle et al., *FEBS* 274: 151-155 (1990); and Blondelle and Houghten in Bristol (Ed.), *Annual Reports in Medicinal Chemistry* pages 159-168 Academic Press, San Diego)). As discussed further below, an antimicrobial peptide also can be an analog of a natural peptide, especially one that retains or enhances amphipathicity.

An antimicrobial peptide incorporated within a conjugate of the invention has low mammalian cell toxicity when not linked to a homing molecule of the invention. Mammalian cell toxicity readily can be assessed using routine assays. For example, mammalian cell toxicity can be assayed by lysis of human erythrocytes in vitro as described in Javadpour et al., supra, 1996. An antimicrobial peptide having low mammalian cell toxicity is not lytic to human erythrocytes or requires concentrations of greater than 100 µM for lytic activity, preferably concentrations greater than 200, 300, 500 or 1000 µM for lytic activity.

It is understood by one skilled in the art of medicinal oncology that these and other agents are useful therapeutic moieties, which can be used separately or together in the conjugates and methods of the invention. It further is understood that a conjugate of the invention can contain one or more of such therapeutic moieties and that additional components can be included as part of the conjugate, if desired. As an example, in some cases it can be desirable to utilize an oligopeptide spacer between the homing molecule and the therapeutic agent (Fitzpatrick and Garnett, *Anticancer Drug Des.* 10:1-9 (1995)).

Staging Tumor Progression

The invention provides a method of staging tumor progression in an individual having or suspected of having a pancreatic premalignant lesion or pancreatic tumor. The method involves: (a) administering to the individual at least one conjugate containing a detectable moiety linked to (i) a peptide or peptidomimetic that selectively homes to vasculature of premalignant pancreas, the peptide or peptidomimetic specifically binding a cognate receptor for CRSRKG (SEQ ID NO:9) or CEYQLDVE (SEQ ID NO:34), or (ii) a peptide or peptidomimetic that selectively homes to pancreatic tumor cells and pancreatic tumor vasculature, the peptide or peptidomimetic specifically binding a cognate receptor for an amino acid sequence selected from CKAAKNK (SEQ ID NO:15), CKGAKAR (SEQ ID NO:19) and VGVGEWSV (SEQ ID NO:35); and (b) detecting the conjugate, wherein detection of the conjugate containing a peptide or peptidomimetic that selectively homes to vasculature of premalignant pancreas indicates a premalignant stage of tumor progression in the individual and wherein detection of the conjugate containing a peptide or peptidomimetic that selectively homes to pancreatic tumor cells and pancreatic tumor vasculature indicates a malignant stage of tumor progression in the individual. Exemplary moieties useful in this method are described herein above.

A stage of a tumor refers to the degree of progression of a tumor. A premalignant stage of tumor progression in a tissue means precancerous state of the tissue, which can be characterized, for example, by abnormal tissue structural and functional changes in comparison to a normal state of the tissue. Such changes are described in the art, for example, as metaplasia, dysplasia, hyperplasia, carcinoma in situ, angiogenic and the like, depending on the degree of structural and/or functional changes. Histological and biochemical changes characteristic of precancerous tissues depend upon the type of tumor and can be determined by those skilled in the art. A malignant stage of tumor progression means that the tumor is established, as indicated by, for example, increased proliferation rate compared to normal. Various stages of tumor development are well known to those of skill in the art, as exemplified in Markman, "Basic Cancer Medicine," Saunders, (ed. Zorab, R.) (1997). For example, malignant cancers can be staged into three general stages—localized, regional spread, and distant spread. Cancers also can be staged using the TNM system, which considers the extent of direct spread within affected and nearby tissues, the extent of spread to nearby lymph nodes, and the extent of spread to distant organs. Based on these features, spread of cancers can be summarized by assigning Roman numerals from 0 through IV. Those skilled in the art can select an appropriate staging system for a particular type of cancer.

Routes of Administration

It is understood that a variety of routes of administration are useful in the methods of the invention. Such routes encompass systemic and local administration and include, without limitation, oral administration, topical application, intravenous injection, intraperitoneal injection, intramuscular injection, subcutaneous injection, transdermal diffusion or electrophoresis, local injection, and extended release delivery devices including locally implanted extended release devices such as bioerodible or reservoir-based implants.

The following examples are intended to illustrate but not limit the present invention.

EXAMPLE I

Isolation of Stage-Specific Phage

This example describes the isolation of phage that selectively home to premalignant lesions and malignant tumors.

To isolate peptides that selectively home to premalignant lesions and malignant tumors, the RIP1-Tag2 mouse model was used. RIP1-Tag2 mice develop multifocal angiogenic islet progenitors and then solid tumors in a stepwise manner, such that at 12 weeks of age, each mouse typically has approximately 50 angiogenic islets and 2-6 small tumors. Using 12 week-old mice, phage that bind to angiogenic islet progenitors and/or tumors in the same mouse were identified.

The generation of RIP1-Tag2 mice is described, for example, in Hanahan, *Nature* 315:115-122 (1985). Angiogenic islets were isolated from 8 and 12 week old RIP1-Tag2 mice by collagenase digestion of the excised pancreas, and selected based on their red, hemorrhagic appearance (Parangi et al. *Cancer Res.* 55: 6071-6076 (1995)). Tumors were microdissected from the excised pancreas of 12-week old RIP1-Tag2 mice and the surrounding exocrine tissue carefully removed. The synchronicity of tumorigenesis in the RIP1-Tag2 model allowed for simultaneous isolation of angiogenic islets and tumors from the same mouse at 12 weeks of age, such that homing of individual phage to different stages in tumor progression in an individual mouse/pancreas could be compared.

In order to enrich for phage that bind to RIP1-Tag2 target cells (endothelial, perivascular and tumor cells), a pre-selection step was performed on cell suspensions prepared from premalignant and malignant pancreatic lesions. Pre-selection methods are described, for example, in Laakkonen et al. *Nat. Med.* 8:751-755 (2002) and Porkka et al. *Proc. Natl. Acad. Sci. USA* 99, 7444-7449 (2002). The pre-selection step involved two rounds of ex vivo selection from a $CX_7C$ peptide library on cell suspensions from angiogenic islets or solid tumors. For the ex vivo selections, cell suspensions were prepared from the different RIP1-Tag2 lesions in 12 week old RIP1-Tag2 mice and incubated overnight at 4° C. with $10^9$ plaque forming units (p.f.u.) of a T7 phage (Novagen) displaying the $CX_7C$ peptide library. The cells were washed to remove unbound phage, and bound phage were rescued and amplified in *E. coli*. This procedure resulted in enrichment in phage that bound to tumor, endothelial and other stromal cells present in the suspension.

Ex vivo screening yielded phage pools that bound 7- to 8-fold over a control, non-recombinant phage to their respective target cells (see FIG. 1A). These enriched phage pools were used in subsequent in vivo rounds to select for phage that homed specifically to either angiogenic islets or tumors in RIP1-Tag2 mice.

For in vivo selection of phage that home specifically to premalignant lesions and malignant tumors, the ex vivo pre-selected phage pool was injected intravenously into 12 week old RIP1-Tag2 mice through the tail vein, allowed to circulate for 7 minutes and heart-perfused with PBS to remove unbound intravascular phage. As the vasculature is preferentially available for the phage to bind in this selection, there is an enrichment of phage that bind to the endothelium of the target tissue.

The RIP1-Tag2 lesions and control tissues (brain, kidney, spleen, lung, 'white' pancreas lacking hemorrhagic lesions and liver were excised to allow for comparison of homing efficiencies. Cell suspensions were prepared by mechanical disruption of the tissues. Tissues were washed to remove unbound phage, and the bound phage rescued and amplified by adding *E. coli*. The phage pool was re-injected into mice at a similar disease stage, and the cycle repeated. In each experiment, non-recombinant control phage were used as a control for relative selectivity.

Three rounds of in vivo selection on angiogenic islets resulted in a phage pool that selectively homed to angiogenic islets. The homing to angiogenic islets was 7-fold higher than to tumors in the same mouse (FIG. 1B). There was no homing to control organs. The tumor selection yielded a pool that showed an 8-fold preference for tumors versus angiogenic islets in the same mouse following two rounds of in vivo selection (FIG. 1C).

Sets of 96 phage clones were randomly collected from each homing phage population that selectively homed to premalignant angiogenic islets or pancreatic tumor cells. Peptide-encoding DNA inserts from collected phage clones were amplified by PCR, and the PCR products sequenced. Phage representing the most frequently appearing peptide motifs were individually tested for their ability to selectively home to the lesions on which they were selected, relative to other stages in the tumorigenesis pathway and to control organs. Six of the phage selected for further analysis were from the tumor screen (referred to as KAA, RGR, RSR, VGVA, VGVG and KAR), and one (EYQ) was picked from the angiogenic screen. Peptide sequences corresponding to each of these peptide motifs are shown in Table 1.

The identified RIP1-Tag2 homing phage fell into three classes based on their ability to home either to angiogenic islets or to tumors in vivo (FIG. 1D) and their ex vivo binding patterns. The identified classes were tumor-selective phage (KAA, KAR and VGVG); angiogenic islet-selective phage (RSR and EYQ); and phage that home to both types of lesion (VGVA and RGR) (See Table 1 for peptide sequences). Some of the selected peptides that share similar peptide motifs also display similar homing patterns. For example, KAA and KAR (CKAAKNK (SEQ ID NO:15) and CKGAKAR (SEQ ID NO:19)=XBXXBXB, where B represents basic residues and X denotes uncharged residues) both preferentially home to tumors over angiogenic islets. However, other related peptides such as RGR and RSR (CRGRRST (SEQ ID NO:5) and CRSRKG (SEQ ID NO:9)=XBXBBX) have quite different homing capabilities.

TABLE I

| Peptide | Peptide sequence (SEQ ID NO:) | | Extended motif (SEQ ID NO:) | | Mouse protein with the motif | Accession number |
|---|---|---|---|---|---|---|
| RGR | CRGRRST | (5) | RGRRS | (2) | PDGF-B | P31240 |
|  |  |  | RGRR | (1) | Stromal interaction molecule 2 | Q9P246 |
| RSR | CRSRKG | (9) | CRSR-G | (38) | Cadherin EGF LAG receptor 1 | O35161 |
| KAA | CKAAKNK | (15) | CKA-K | (39) | WNT-2 | NP076142 |
| KAR | CKGAKAR | (19) | CKGAKA | (20) | Collagen XII | Q60847 |
|  |  |  | AKAR | (16) | Collagen XII | Q60847 |
|  |  |  | GAKAR | (17) | Claudin 9 | Q9Z0S7 |
| VGVA | FRVGVADV | (27)) | F-VGVADV | (40) | Collagen XII | Q60847 |
|  |  |  | RVGV | (21) | Collagen XII | Q60847 |
| EYQ | CEYQLDVE | (34) | CEYQL | (28) | Semaphorin 4C | Q64151 |
|  |  |  | YQLDV | (32) | FGFR-1 | P16092 |
|  |  |  | YQLDV | (32) | Tie-1 | Q06806 |

Table 1. Candidate mouse proteins sharing motifs with peptides. Peptides were analyzed using a BLAST (NCBI) search against the SWISSPROT database, using the option for short nearly exact matches, to identify mouse proteins with homologous sequences.

Thus, a combination of ex vivo and in vivo phage screening was used to obtain peptides that selectively home to either premalignant pancreatic tissue, malignant pancreatic tissue or both premalignant and malignant pancreatic tissue.

EXAMPLE II

Tumor Stage-Specific Homing of Fluorescein-Conjugated Peptides In Vivo

This example describes that selective phage homing was due to the displayed peptide.

To confirm that selective phage homing was due to the displayed peptide sequences, localization of fluorescein-conjugated peptides after intravenous injection was observed. For this analysis, one peptide from each homing class was selected as follows: CRSRKG (SEQ ID NO:9), referred to as RSR (angiogenic-selective), CKAAKNK (SEQ ID NO:15), referfed to as KAA (tumor-selective) and CRGRRST (SEQ ID NO:5), referred to as RGR (angiogenic- and tumor-homing). Eight week old RIP1-Tag2 mice were used to examine peptide localization during the angiogenic switch, and 12-week old RIP1-Tag2 mice were used to visualize both angiogenic islets and tumors.

Fluorescein-conjugated peptides corresponding to phage insert sequences were synthesized using an automated peptide synthesizer with standard solid-phase fluorenylmethoxycarbonyl (Fmoc) chemistry. 100 mg of each individual fluorescein-conjugated peptide was injected intravenously into the tail vein of RIP1-Tag2 mice at 8 or 12 weeks of age, and into normal BL/6 mice. The peptide was allowed to circulate for 7 minutes, followed by heart perfusion first with PBS and then with Zn-buffered formalin. The RIP1-Tag2 pancreas and control organs (brain, kidney, liver, lung and spleen) were removed, fixed for one hour in formalin, washed with 1×PBS, placed in 30% sucrose for several hours, washed with 1×PBS, and embedded in OCT (Tissue-Tek). Each peptide was injected into at least three individual RIP1-Tag2 or normal mice at each of the different stages. To examine the localization of injected fluorescein-conjugated peptides, frozen sections (10 mm thick) were cut on a cryostat, mounted in Vectashield Mounting Medium with DAPI (Vector Laboratories) and visualized under an inverted fluorescent microscope or a confocal microscope (Zeiss LSM 510 META).

Figure 2:
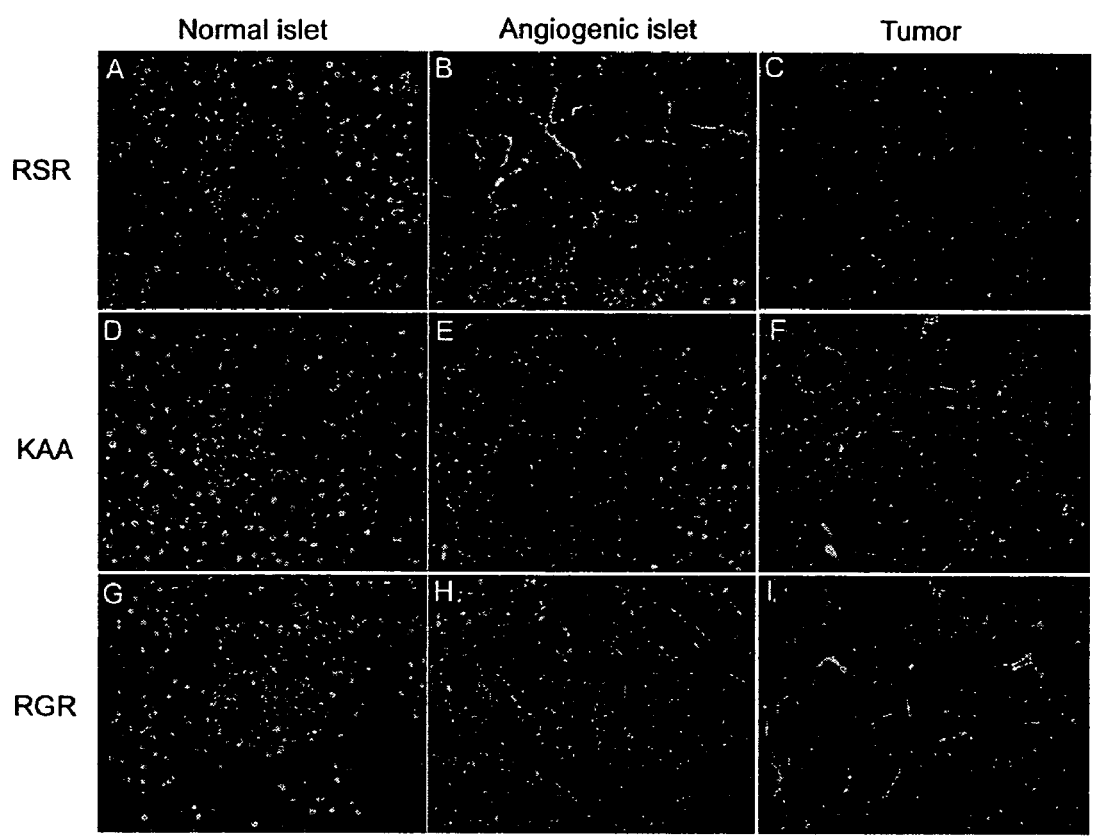
FIG. 2 shows tumor progression stage-specific homing of fluorescein-conjugated peptides in RIP1-Tag2 model. Visualization of an angiogenic islet-selective peptide (RSR) homing is shown in normal islet (A), angiogenic islet (B), and tumor (C). Homing profiles are also shown for a tumor-selective peptide (KAA) to normal islet (D), angiogenic islet (E), and tumor (F), as well as of a peptide (RGR) that homes to both angiogenic islets and tumors (G) normal islet (H) angiogenic islet, and (I) tumor. Control tissues were (J) kidney, (K) brain, and (L) liver. Magnification shown is 200×.
Figure 2:

FIG. 2 shows specific homing of RSR, KAA and RGR peptides to normal islets, angiogenic islets and tumors. Visualization of angiogenic islet-selective peptide RSR homing is shown in normal islet (A), angiogenic islet (B), and tumor (C). Visualization of tumor-selective peptide KAA homing is shown in normal islet (D), angiogenic islet (E), and tumor (F). Visualization of angiogenic islet- and tumor-selective peptide RGR homing is shown in (G) normal islet, (H) angiogenic islet, and (I) tumor. Control tissues from a RIP1-Tag2 mouse injected with fluorescein-conjugated RGR-peptide are shown in (J) kidney; (K) brain, and (L) liver. Similar absence of fluorescence in control tissues was observed for the other injected peptides, indicative of a lack of homing to control tissues.

As can be seen in FIG. 2, RSR shows abundant accumulation in RIP1-Tag2 angiogenic islets, but little or no localization in tumors or normal islets. KAA shows abundant localization in RIP1-Tag2 tumors but little or no localization in angiogenic islets, or normal islets. Finally, RGR localizes in both RIP1-Tag2 angiogenic islets and tumors but little or no localization in normal islets. Fluorescence detected in kidney was assessed as non-specific, likely resulting from uptake from glomerular filtrate (FIG. 2J). Unexpectedly RSR, which was selected from the tumor phage screening, preferentially bound to angiogenic islets. This result indicates that the epitope bound by RSR is present both in tumors and angiogenic islets, but is more abundant in angiogenic islets. The observed peptide localization profiles in each case were similar to localization profiles of the cognate phage (compare FIG. 1D and FIG. 2), with each peptide falling into the same of the three homing classes. In addition, control peptides did not show specific homing to any of the RIP1-Tag2 lesional stages or to a number of normal tissues Thus, selective homing was confirmed to be due to the displayed peptide sequences, rather than the phage.

EXAMPLE III

Co-Localization of Fluorescein-Conjugated Peptides with Vascular Markers in RIP1-Tag2 Premalignant and Malignant Lesions This example describes co-localization of fluorescein-conjugated peptides with vascular markers.

To confirm that intravenous administration of phage libraries selects for phage carrying peptides that bind to endothelial molecules specific for the target vasculature, tissues were collected following i.v. infusion with the various fluorescein-conjugated peptides, sectioned, and evaluated with endothelial cell markers.

For immunohistochemistry, frozen slides were pre-incubated with blocking buffer (1×PNB from NEN Biosciences) for one hour, washed several times in 1×PBS and incubated with the primary antibody of interest overnight at 4° C. The cell-specific antibodies used were rat monoclonal anti-mouse CD31 (1:200; BD Pharmingen), rat monoclonal anti-mouse MECA-32 (1:200; BD Pharmingen), rabbit polyclonal anti-mouse NG2 (1:200; Chemicon), and rat monoclonal anti-mouse PDGFRb (CD140b) (1:200; eBioscience). The corresponding secondary antibodies; Cy-3 donkey anti-rabbit IgG and Rhodamine Red donkey anti-rat IgG (Jackson ImmunoResearch), were used at a 1:200 dilution and incubated for one hour at room temperature. The following species-matched immunoglobulins were used as negative controls; rabbit IgG (Vector Laboratories) and rat IgG (Jackson ImmunoResearch) at a 1:200 dilution. The slides were washed several times in 1×PBS and mounted in Vectashield Mounting Medium with DAPI (Vector Laboratories). Hematoxylin and eosin (H&E) staining was performed for histological grading of adjacent sections by standard methods, and lesions were graded as previously described (Lopez and Hanahan, 2002).

Figure 3:
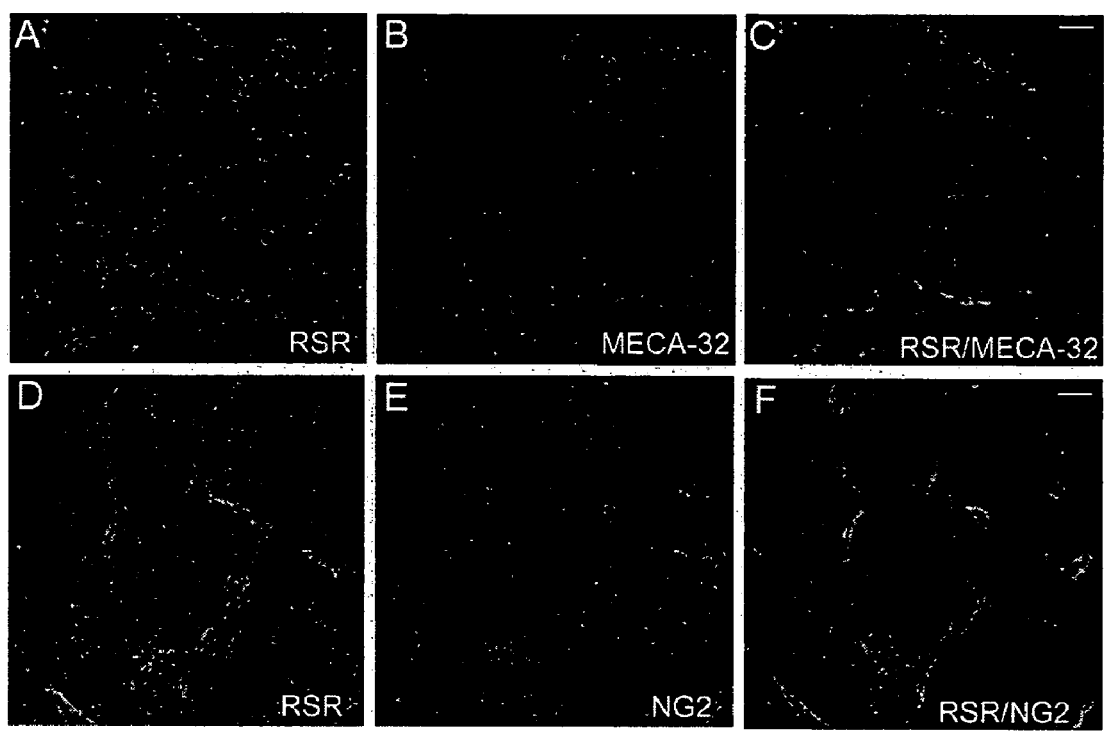
FIG. 3 shows co-localization of fluorescein-conjugated peptides with vascular markers in RIP1-Tag2 islet lesions. RSR peptide localization in an angiogenic islet is shown in panel A and D, while co-staining for MECA-32 and the merge are shown in panels B and C. Co-staining for NG2 is shown in panel E, with the merge in panel F. KAA peptide localization in a tumor is shown in panels G and J, while co-staining for MECA-32 and the merge are shown in panels H and I. Co-staining for NG2 is shown in panel K, with the merge in panel L. RGR peptide localization in an angiogenic islet is shown in panel M and P, while co-staining for MECA-32 and the merge are shown in panels N and O. Co-staining for NG2 is shown in panel Q, with the merge in panel R. Scale bar shown is 10 mm.
Figure 3:
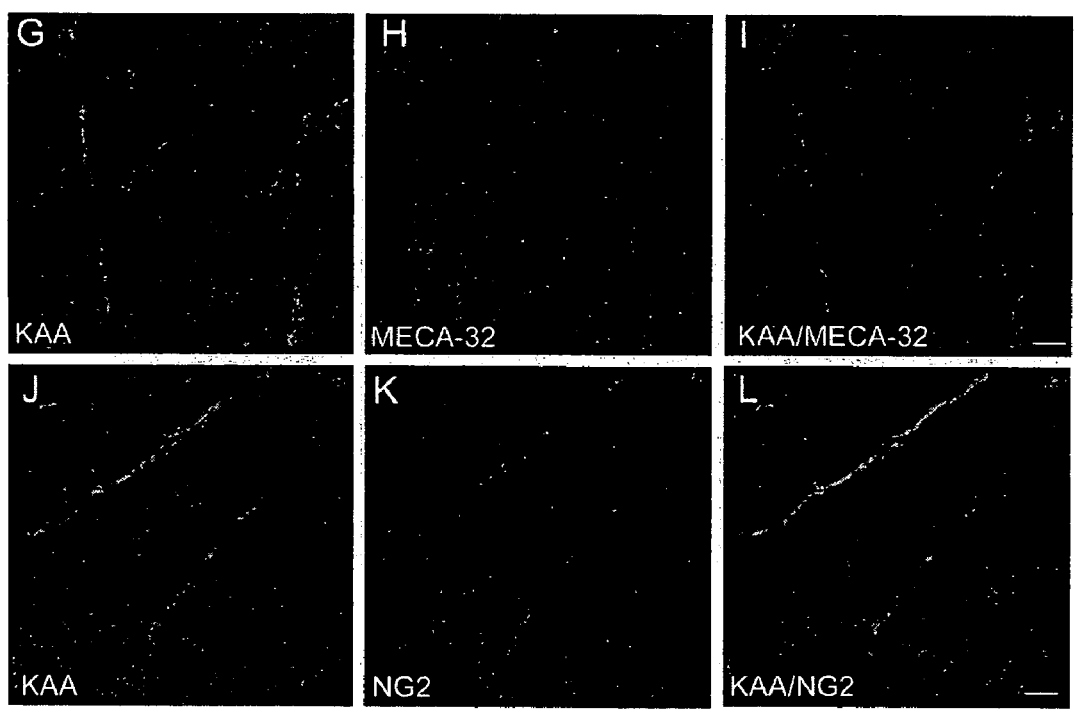
Figure 3:
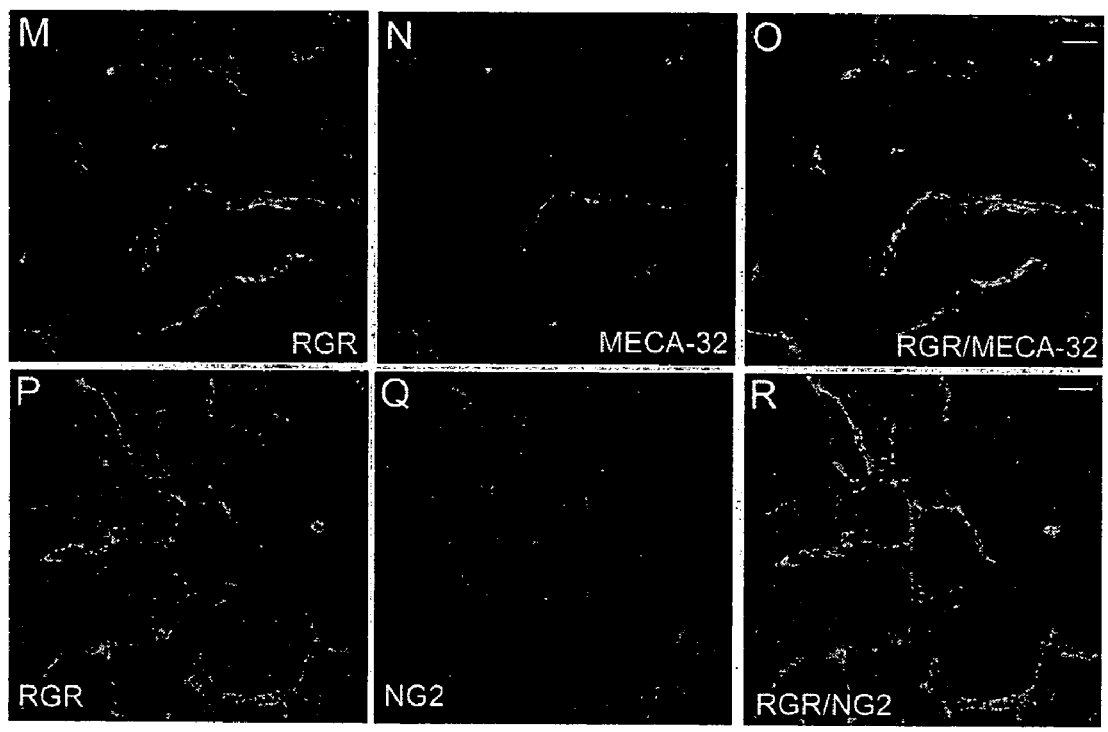

The primary analysis involved immunostaining with a mouse pan-endothelial cell antigen (MECA-32) antibody that recognizes a dimer of 50-55 kDa protein subunits present on all endothelial cells (Hallman et al., 1995; Leppink et al., 1989) (FIG. 3 B,C,H,I,N,O). Additional analyses involved immunostaining to reveal CD31/PE-CAM, or systemic infusion of a fluorescent-labeled lectin that binds to the endothelial lumen. In addition, tissue sections from peptide-infused mice were stained with an antibody recognizing NG2, a marker of the neovascular pericytes (Schlingemann et al., 1990, 1991) (FIG. 3 E,F,K,L,Q,R).

RSR peptide localization in an angiogenic islet is shown in panel A and D (green), while co-staining for MECA-32 (red) and the merge are shown in panels B and C. Co-staining for NG2 (red) is shown in panel E, with the merge in panel F. KAA peptide localization in a tumor is shown in panels G and J (green), while co-staining for MECA-32 (red) and the merge are shown in panels H and I. Co-staining for NG2 (red) is shown in panel K, with the merge in panel L. RGR peptide localization in an angiogenic islet is shown in panel M and P (green), while co-staining for MECA-32 (red) and the merge are shown in panels N and O. Co-staining for NG2 (red) is shown in panel Q, with the merge in panel R.

As is shown in FIG. 3, all three peptides (RSR, KAA, and RGR) show some co-localization both with endothelial cell and pericyte markers, indicating that each homes to and binds moieties associated with both cell types (FIG. 3). There was no co-localization of these peptides with MECA-32 or NG2 in the adjacent exocrine pancreas or in normal pancreatic islets.

Homing of peptides representing all three classes of binding specificity to both pericytes and endothelial cells was unexpected. This result supports studies indicating that RIP1-Tag2 tumor vasculature is leaky, as evidenced by extensive micro-hemorrhaging (Parangi et al., 1995) and morphometric analysis (Hashizume et al., 2000; Morikawa et al., 2002; Thurston et al., 1998), by indicating that a circulating phage pool can have access to the extra-luminal vascular microenvironment, where receptors on pericytes and in the extracellular matrix can be accessible. The ex vivo pre-selection step used to enrich for RIP1-Tag2 specific targets similarly can select for non-luminal endothelial binding partners.

Thus, this example shows that peptides that selectively home to premalignant, malignant or both premalignant and malignant pancreatic tissue, co-localize with endothelial cell and pericyte markers.

EXAMPLE IV

Tumor Specificity of Homing Phage and Peptides

This example describes the specificity of in vivo phage homing to angiogenic islets and/or tumors in the pancreas, and to the angiogenic vasculature in other tumor types.

To determine whether phage identified to home to pancreatic tumors also home to other types of tumors, these phage were tested using animals having various types of tumors, including bTC3 subcutaneous tumor and MDA MB-435 subcutaneous tumor. bTC3 transplant tumors arise following subcutaneous inoculation of nude mice with cultured islet tumor-derived (bTC3) cells (Efrat et al., 1988). Since the vasculature of a subcutaneously grown bTC3 tumor derives from skin, we also tested another subcutaneous transplant tumor, arising from inoculation of the MDA-MB-435 human breast carcinoma cell line. Finally, K14-HPV16 mice, another well-studied transgenic mouse model of cancer that develop tumors of the squamous epithelial cells of the skin (Arbeit et al., 1994; Coussens et al., 1996), was used to compare RIP1-Tag2 islet tumors to a tumor with similar multistage pathogenesis arising in a different tissue.

Tumors were dissected from the ear or chest of K14-HPV16 mice. For the bTC3 allograft models, $10^6$ bTC3 tumor cells (Efrat et al., 1988) were inoculated under the skin of the rear flank of nu/nu mice in a BALB/c background and allowed to grow until approximately 5 mm in size, and then used for experimental analysis. MDA-MB-435 xenograft models were generated by inoculating $10^6$ tumor cells subcutaneously in the chest of nu/nu Balb/c mice. Tumors were used for the homing/binding experiments at 8-12 weeks after injection of the tumor cells.

FIG. 4A is bar graph showing homing efficiency of individual phage to a pancreatic tumor in a RIP1-Tag2 mouse, a bTC3-derived subcutaneous transplant tumor in a nude mouse, and a squamous cell carcinoma in a K14-HPV16 mouse.

FIG. 4B is a table summarizing the relative homing of fluorescein-conjugated peptides to different tumor models. +++ indicates strong homing, as revealed by the fluorescent intensity of i.v. injected peptide, ++ indicates moderate homing, + indicates weak homing, − indicates absence of homing.

FIGS. 4C, D and E show representative images of fluorescein-conjugated KAR peptide homing to a RIP1-Tag2 pancreatic islet tumor (C); a bTC3 subcutaneous tumor (D); and an MDA subcutaneous tumor (E).

As indicated by FIG. 4A, the relative homing efficiencies in the various tumor models of the phage from the RIP1-Tag2 tumor screen fall broadly into two categories: those that selectively home to RIP1-Tag2 tumors (KAA, RGR, VGVA), and those that show a more general homing to other tumors in addition to RIP1-Tag2 (VGVG, KAR). The phage homing data were supported by i.v. injection of fluorescein-conjugated peptides corresponding to the phage, as shown in FIGS. 4C, D and E.

Thus, this example shows that certain peptides selectively home to pancreatic tumors while others selectively home to other types of tumors in addition to pancreatic tumors.

EXAMPLE V

Identification of Receptors for RGR Peptides

This example describes the identification of candidate vascular receptors for peptides by sequence homology comparisons.

The set of peptides that selectively home to angiogenic premalignant lesions in the pancreas were used in database searches to identify mouse proteins containing sequences homologous to peptide sequences. Table 1 lists candidate proteins of interest that contain such homologies. Many of the candidate proteins have been previously associated with the vasculature, and could correspond to putative ligands mimicked by the phage-displayed peptides. One protein, collagen XII, was found to share homology with two peptides; KAR (CKGAKAR; SEQ ID NO:19) and VGVA (FRVGVADV; SEQ ID NO:27). It is interesting to note that collagen XII was also identified by gene expression profiling as a gene that is over-expressed in tumor endothelial cells (St. Croix et al., 2000; and mendel.imp.univie.ac.at/SEQUENCES/TEMS/mainpgs/temtable.html).

Another homology was observed for the RGR peptide (CRGRRST; SEQ ID NO:5). Specifically, as is shown in Table 1, the sequence RGRRS is contained in the B chain of the pro-form of platelet-derived growth factor (PDGF-B), a known ligand for the transmembrane receptor tyrosine kinase PDGFRβ. The RGR sequence homology spans the pro-peptide cleavage site of pro-PDGF-B (Johnsson et al., 1984). Therefore, PDGFRβ was considered a candidate receptor for the RGR peptide.

To confirm that the RGR peptide binds specifically to PDGFRβ, phage displaying this peptide were incubated with 293T cells overexpressing PDGFRβ. Recombinant 293T cells were prepared by transfecting with plasmids encoding PDGFRβ or VEGFR-2 (Borges et al., 2000) using Fugene transfection reagent (Roche Diagnostics). Briefly, 10 μg of plasmid was mixed with 700 μl of DMEM without serum and 30 μl of Fugene reagent, and incubated for 15 minutes at room temperature before adding the mixture to the cells. Forty-eight hours post-transfection the cells were detached from the culture plates using EDTA and washed once with PBS. Recombinant phage displaying the RSR, RGR peptides and control nonrecombinant phage (about 1×10⁹ pfu) were incubated with the transfected cells for 2 hours at 4° C., followed by 5 washes with 1% BSA in PBS to remove the unbound phage. The bound phage were rescued by adding bacteria, and the binding efficiencies were determined by plaque assay.

Figure 5A:
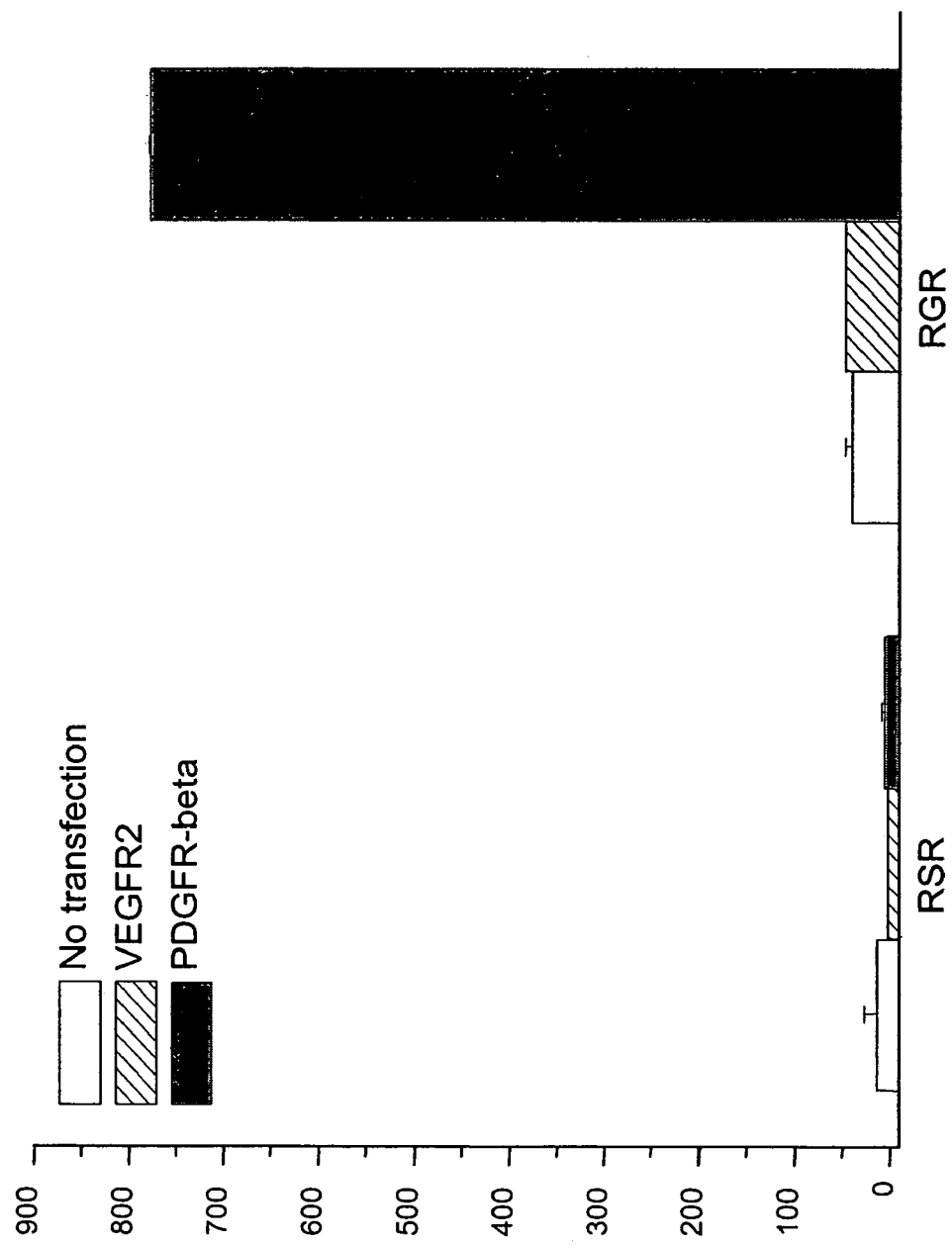
FIG. 5 shows binding of RGR phage to PDGFRβ. (A) Bar graph showing binding of RGR or RSR phage to 293 cells transfected with either the PDGFRβ, VEGFR2, or non-transfected cells. (B) Co-localization of fluorescein-conjugated RGR-peptide (a) with the PDGFRβ antibody (b) and merged images (c, d) in RIP1-Tag2. Magnification shown is 400×.
Figure 5B:
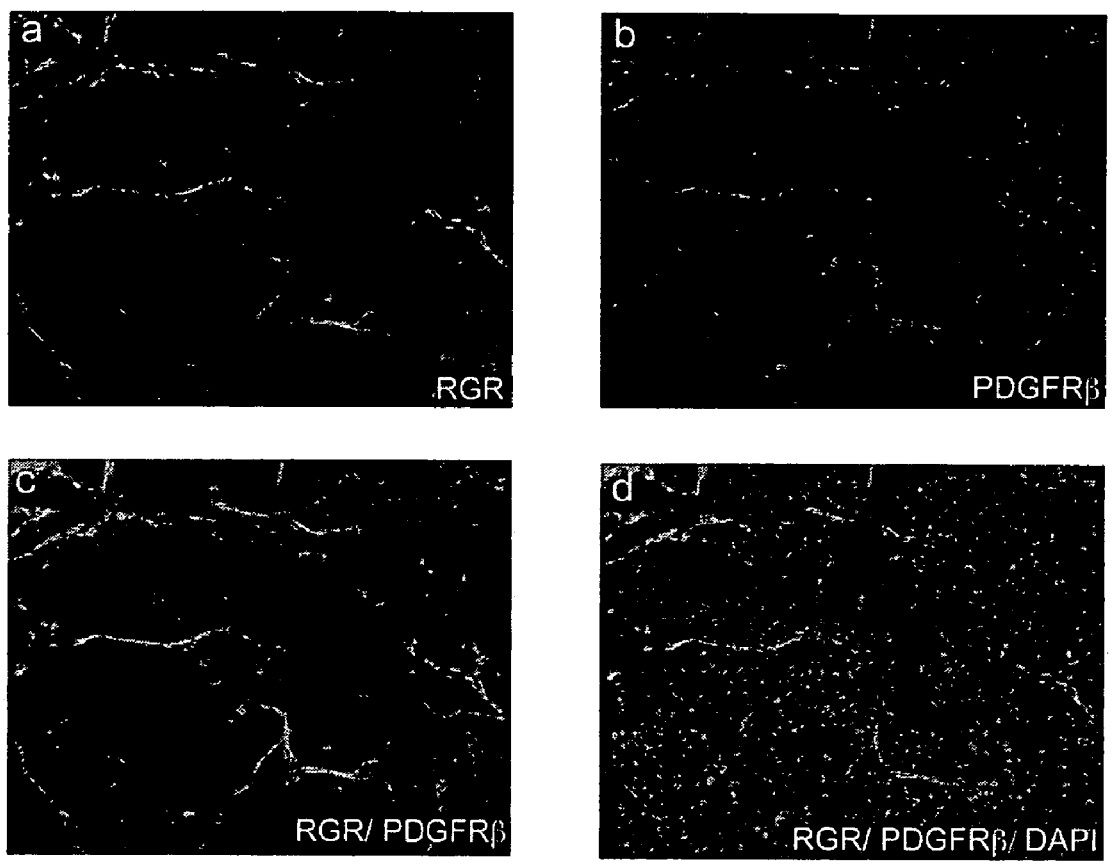

The results of these studies are shown in FIG. 5. FIG. 5A is a bar graph showing binding of RGR or RSR phage to 293 cells transfected with either PDGFRβ, VEGFR2, or non-transfected cells. FIG. 5B shows co-localization of fluorescein-conjugated RGR-peptide (panel a, green) with the PDGFRβ antibody (panel b, red) and merged images (panels c and d) in RIP1-Tag2.

As shown in FIG. 5, binding of RGR phage was 20-fold more efficient to PDGFRβ-transfected cells than non-transfected cells. In contrast, no binding above background was detected toward cells transfected with vascular endothelial growth factor receptor 2 (VEGFR2) (FIG. 5A). Moreover, RSR phage, which has a peptide sequence similar to RGR, displayed no specific binding was observed either to PDGFRβ or VEGFR2 transfected cells (FIG. 5A). The association of RGR with PDGFRβ was confirmed when intravenously injected fluorescein-conjugated RGR peptide was shown to co-localize with PDGFRβ visualized by subsequent immunostaining of tissue sections from RIP1-Tag2 tumors. Merging of the RGR-FITC image (FIG. 5B, panel a) with the antibody staining for PDGFRβ (FIG. 5B, panel b) revealed almost complete co-localization (FIG. 5B, panels c and d). These results indicate that PDGFRβ is a receptor for the RGR peptide.

Thus, this example shows that PDGFRβ is a receptor for the RGR peptide (CRGRRST; SEQ ID NO:5).

All journal articles, references and patent citations provided above, in parentheses or otherwise, whether previously stated or not, are incorporated herein by reference in their entirety.

Although the invention has been described with reference to the examples provided above, it should be understood that various modifications can be made without departing from the spirit of the invention. Accordingly, the invention is limited only by the following claims.

What is claimed is:

1. An isolated peptide having a length of less than 60 amino acid residues and comprising the amino acid sequence selected from CRGRRST (SEQ ID NO:5), CRSRKG (SEQ ID NO:9), and CKAAKNK (SEQ ID NO:15), wherein said peptide selectively homes to premalignant pancreatic vasculature, malignant pancreatic vasculature or pancreatic tumor cells.

2. The peptide of claim 1, having a length of less than 40 amino acid residues.

3. The peptide of claim 1, having a length of less than 20 amino acid residues.

4. The peptide of claim 1, having a length of less than 10 amino acid residues.

5. A conjugate, comprising a therapeutic moiety linked to a peptide that selectively homes to vasculature of premalignant pancreas, said peptide comprising the amino acid sequence CRSRKG (SEQ ID NO:9); wherein said peptide has a length of less than 100 residues.

6. The conjugate of claim 5, wherein said peptide has a length of less than 50 residues.

7. The conjugate of claim 5, wherein said peptide has a length of less than 25 residues.

8. A conjugate, comprising a therapeutic moiety linked to a peptide that selectively homes to vasculature of premalignant pancreas, wherein said peptide binds specifically to a cognate receptor for SEQ ID NO:9, wherein said peptide has a length of less than 100 residues.

9. The conjugate of claim 8, wherein said peptide has a length of less than 50 residues.

10. The conjugate of claim 8, wherein said peptide has a length of less than 25 residues.

11. A conjugate, comprising a therapeutic moiety linked to a peptide that selectively homes to pancreatic tumor cells or pancreatic tumor vasculature, said peptide comprising the amino acid sequence CKAAKNK (SEQ ID NO:15), wherein said peptide has a length of less than 100 residues.

12. The conjugate of claim 11, wherein said peptide has a length of less than 50 residues.

13. The conjugate of claim 11, wherein said peptide has a length of less than 25 residues.

14. A conjugate, comprising a therapeutic moiety linked to a peptide that selectively homes to pancreatic tumor cells or pancreatic tumor vasculature, wherein said peptide binds specifically to a cognate receptor for SEQ ID NO:15, wherein said peptide has a length of less than 100 residues.

15. The conjugate of claim 14, wherein said peptide has a length of less than 50 residues.

16. The conjugate of claim 14, wherein said peptide has a length of less than 25 residues.

17. The conjugate of claim 14, wherein said therapeutic moiety is an angiogenic inhibitor.

18. The conjugate of claim 17, wherein said angiogenic inhibitor is selective for mature tumor vasculature.

19. The conjugate of claim 14, wherein said therapeutic moiety is a cytotoxic agent.

20. A conjugate, comprising a therapeutic moiety linked to a peptide that selectively homes to premalignant or malignant pancreatic vasculature, said peptide comprising the amino acid sequence CRGRRST (SEQ ID NO:5), wherein said peptide has a length of less than 100 residues.

21. A conjugate, comprising a therapeutic moiety linked to a peptide that selectively homes to premalignant or malignant pancreatic vasculature, wherein said peptide binds specifically to a cognate receptor for SEQ ID NO:5, wherein said peptide has a length of less than 100 residues.

22. The conjugate of claim 21, wherein said peptide has a length of less than 50 residues.

23. The conjugate of claim 21, wherein said peptide has a length of less than 25 residues.

24. The conjugate of claim 21, wherein said therapeutic moiety is an angiogenic inhibitor.

25. The conjugate of claim 24, wherein said angiogenic inhibitor is selective for mature tumor vasculature.

26. The conjugate of claim 21, wherein said therapeutic moiety is a cytotoxic agent.

27. The conjugate of claim 24, wherein said cognate receptor is PDGFβ receptor.

28. A multivalent conjugate, comprising a therapeutic moiety linked to at least two peptides that selectively home to vasculature of premalignant pancreas, each of said peptides comprising the amino acid sequence CRSRKG (SEQ ID NO:9).

29. A multivalent conjugate, comprising a therapeutic moiety linked to at least two peptides that selectively home to vasculature of premalignant pancreas, wherein each of said peptides binds specifically to a cognate receptor for SEQ ID NO:9.

30. A multivalent conjugate, comprising a therapeutic moiety linked to at least two peptides that selectively home to pancreatic tumor cells or pancreatic tumor vasculature, each of said peptides comprising the amino acid sequence CKAAKNK (SEQ ID NO:15).

31. A multivalent conjugate, comprising a therapeutic moiety linked to at least two peptides that selectively home to premalignant or malignant pancreatic vasculature, wherein each of said peptides binds specifically to a cognate receptor for the amino acid sequence CKAAKNK (SEQ ID NO:15).

32. A multivalent conjugate, comprising a therapeutic moiety linked to at least two peptides that selectively home to premalignant or malignant vasculature, each of said peptides comprising the amino acid sequence CRGRRST (SEQ ID NO:5).

33. A multivalent conjugate, comprising a therapeutic moiety linked to at least two peptides that selectively home to pancreatic tumor cells or pancreatic tumor vasculature, wherein each of said peptides binds specifically to a cognate receptor for the amino acid sequence CRGRRST (SEQ ID NO:5).

34. The peptide of claim 1, said amino acid sequence is CRGRRST (SEQ ID NO:5).

35. The peptide of claim 1, said amino acid sequence is CRSRKG (SEQ ID NO:9).

36. The peptide of claim 1, said amino acid sequence is CKAAKNK (SEQ ID NO:15).

37. The peptide of claim 34, having a length of less than 40 amino acid residues.

38. The peptide of claim 34, having a length of less than 20 amino acid residues.

39. The peptide of claim 34, having a length of less than 10 amino acid residues.

40. The peptide of claim 35, having a length of less than 40 amino acid residues.

41. The peptide of claim 35, having a length of less than 20 amino acid residues.

42. The peptide of claim 35, having a length of less than 10 amino acid residues.

43. The peptide of claim 36, having a length of less than 40 amino acid residues.

44. The peptide of claim 36, having a length of less than 20 amino acid residues.

45. The peptide of claim 36, having a length of less than 10 amino acid residues.

* * * * *

UNITED STATES PATENT AND TRADEMARK OFFICE
CERTIFICATE OF CORRECTION

PATENT NO. : 7,598,341 B2 Page 1 of 1
APPLICATION NO. : 10/977367
DATED : October 6, 2009
INVENTOR(S) : Hanahan et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 568 days.

Signed and Sealed this

Twenty-eighth Day of September, 2010

David J. Kappos
*Director of the United States Patent and Trademark Office*